US007820157B2

(12) United States Patent
Hall et al.

(10) Patent No.: US 7,820,157 B2
(45) Date of Patent: *Oct. 26, 2010

(54) TRANSGENE DELIVERING RETROVIRUS TARGETING COLLAGEN EXPOSED AT SITE OF TISSUE INJURY

(75) Inventors: Frederick L. Hall, Glendale, CA (US); Erlinda Maria Gordon, Glendale, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/016,847

(22) Filed: Jan. 18, 2008

(65) Prior Publication Data

US 2008/0241905 A1 Oct. 2, 2008

Related U.S. Application Data

(63) Continuation of application No. 11/014,629, filed on Dec. 15, 2004, now Pat. No. 7,347,998, which is a continuation of application No. 09/904,923, filed on Jul. 13, 2001, now Pat. No. 6,864,082, which is a continuation of application No. 08/837,223, filed on Apr. 10, 1997, now abandoned.

(51) Int. Cl.
A01N 63/00 (2006.01)
(52) U.S. Cl. ........................................ 424/93.2; 514/44
(58) Field of Classification Search ................ 424/93.2; 514/44
See application file for complete search history.

(56) References Cited

U.S. PATENT DOCUMENTS

| 5,328,470 | A | | 7/1994 | Nabel et al. |
| 5,354,674 | A | | 10/1994 | Hodgson |
| 5,512,421 | A | | 4/1996 | Burns et al. |
| 5,543,328 | A | | 8/1996 | McClelland et al. |
| 5,591,624 | A | | 1/1997 | Barber et al. |
| 5,643,770 | A | | 7/1997 | Mason et al. |
| 5,681,746 | A | | 10/1997 | Bodner et al. |
| 5,710,022 | A | | 1/1998 | Zhu et al. |
| 5,800,811 | A | | 9/1998 | Hall et al. |
| 5,821,234 | A | | 10/1998 | Dzau |
| 5,824,837 | A | * | 10/1998 | Chen et al. ............ 800/3 |
| 5,985,655 | A | | 11/1999 | Anderson et al. |
| 6,004,798 | A | | 12/1999 | Anderson et al. |
| 6,864,082 | B2 | | 3/2005 | Hall, et al. |
| 7,347,998 | B2 | | 3/2008 | Hall et al. |
| 2002/0173538 | A1 | | 11/2002 | Shiao |

FOREIGN PATENT DOCUMENTS

| EP | 334301 | 9/1989 |
| SE | 503225 | 4/1996 |
| WO | WO 92/06180 A1 | 4/1992 |
| WO | WO 93/00103 A1 | 1/1993 |
| WO | WO 93/09221 A1 | 5/1993 |
| WO | WO 93/14188 A1 | 7/1993 |
| WO | WO 93/20221 A1 | 10/1993 |
| WO | WO 93/25234 A1 | 12/1993 |
| WO | WO 94/06920 A1 | 3/1994 |
| WO | WO 94/10323 A1 | 5/1994 |
| WO | WO 94/11524 A1 | 5/1994 |
| WO | WO 94/12626 A1 | 6/1994 |
| WO | WO 94/27643 A1 | 12/1994 |
| WO | WO 96/30504 A1 | 3/1996 |
| WO | WO 96/23882 A1 | 8/1996 |
| WO | WO 96/31602 A1 | 10/1996 |
| WO | WO 02/18572 A2 | 3/2002 |

OTHER PUBLICATIONS

Barinaga. Step taken toward improved vectors for gene transfer. Science. 1994; 266:1326.
Behrens, et al. Retroviral gene therapy vectors for prevention of excimer laser-induced corneal haze. Invest Ophthalmol Vis Sci. 2002;43(4):968-77.
Chu, et al. Cell targeting with retroviral vector particles containing antibody-envelope fusion proteins. Gene Ther. 1994;1(5):292-9.
Cripps, et al. Phase II randomized study of ISIS 3521 and ISIS 5132 in patients with locally advanced or metastatic colorectal cancer: a National Cancer Institute of Canada clinical trials group study. Clinical Cancer Research. 2002; 8:2188-2192.
Defer, et al. Human adenovirus-host cell interactions: comparative study with members of subgroups B and C. J. Virology. 1990; 64:3661-3673.
Galanis, et al. Delivery systems intended for in vivo gene therapy of cancer: targeting and replication competent viral vectors. Crit Rev Oncol Hematol. 2001; 38(3):177-192.
Gautam, et al. Delivery systems for pulmonary gene therapy. Am J. respir Med. 2002; 1(1):35-46.
Gordon, et al. First clinical experience using a 'pathotropic' injectable retroviral vector (Rexin-G) as intervention for stage IV pancreatic cancer. Int J Oncol. 2004;24(1):177-85.
Gordon, et al. Inhibition of metastatic tumor growth in nude mice by portal vein infusions of matrix-targeted retroviral vectors bearing a cytocidal cyclin G1 construct. Cancer Res. 2000;60(13):3343-7.
Gordon, et al. Le morte du tumour: histological features of tumor destruction in chemo-resistant cancers following intravenous infusions of pathotropic nanoparticles bearing therapeutic genes. Int J Oncol. 2007; 30(6):1297-307.
Gordon, et al. Lesion-targeted injectable vectors for vascular restenosis. Hum Gene Ther. 2001;12(10):1277-87.
Gordon, et al. Pathotropic nanoparticles for cancer gene therapy Rexin-G IV: three-year clinical experience. Int J Oncol. 2006; 29(5):1053-64.

(Continued)

Primary Examiner—Thaian N Ton
Assistant Examiner—Marcia S Noble
(74) Attorney, Agent, or Firm—Wilson Sonsini Goodrich & Rosati

(57) ABSTRACT

A viral or non-viral vector particle having a modified viral surface protein wherein the viral surface protein is modified to include a targeting polypeptide including a binding region which binds to an extracellular matrix component. Such vector particles are useful in delivering genes encoding therapeutic agents to cells located at the site of an exposed extracellular matrix component.

3 Claims, 12 Drawing Sheets

OTHER PUBLICATIONS

Gordon, et al. Systemic administration of a matrix-targeted retroviral vector is efficacious for cancer gene therapy in mice. Hum Gene Ther. 2001;12(2):193-204.

Guibinga, et al. Ligand-modified vesicular stomatitis virus glycoprotein displays a temperature-sensitive intracellular trafficking and virus assembly phenotype. Mol Ther. 2004;9(1):76-84.

Hall, et al. Molecular engineering of matrix-targeted retroviral vectors incorporating a surveillance function inherent in von Willebrand factor. Hum Gene Ther. 2000;11(7):983-93.

Hall, et al. Targeting retroviral vectors to vascular lesions by genetic engineering of the MoMLV gp70 envelope protein. Hum Gene Ther. 1997;8(18):2183-92.

Jones, et al. Antibodies for targeted gene therapy: extracellular gene targeting and intracellular expression. Advanced Drug Delivery Reviews. 1998; 31:153-170.

Kasahara, et al. Tissue-specific targeting of retroviral vetors through ligand-receptor interactions. Science. 1994; 266:1373-1376.

Kozak, et al. Ping-pong amplification of a retroviral vector achieves high-level gene expression: human growth hormone production. J. Virol. 1990; 64(7):3500-3508.

Lenz, et al. Clinical protocol. Tumor site specific phase I evaluation of safety and efficacy of hepatic arterial infusion of a matrix-targeted retroviral vector bearing a dominant negative cyclin G1 construct as intervention for colorectal carcinoma metastatic to liver. Human Gene therapy. 2002; 12:1515-1537.

Marshall, et al. A phase II trial of ISIS 3521 in patients with metastatic colorectal cancer. Clinical Colorectal Cancer. 2004; 4:268-274.

Neda, et al. Chemical modification of an ecotropic mruine leukemia virus results in redirection of its target cell specificity. J. Biol. Chem. 1991; 266(22):14143-14146.

Oza, et al. Phase II study of CGP 69846A (ISIS 5132) in recurrent epithelial ovarian cancer: an NCIC clinical trials group study (NCIC IND.116). Gynecological Oncology. 2003; 89:129-133.

Salmons, et al. Targeting of retroviral vectors for gene therapy. Human Gene Therapy. 1993; 4:129-141.

Scanlon, K. J. Anti-genes: siRNA, ribozymes and antisense. Curr Pharm Biotech. 2004; 5:415-420.

Skotzko, et al. Retroviral vector-mediated gene transfer of antisense cyclin G1 (CYCG1) inhibits proliferation of human osteogenic sarcoma cells. Cancer Research. 1995; 55:5493-5498.

Soneoka, et al. A transient three-plasmid expression system for the production of high titer retroviral vectors. Nucleic Acids Res. 1995;23(4):628-33.

Song, et al. Phase I/II evaluation of safety and efficacy of a matrix-targeted retroviral vector bearing a dominant negative cyclin G1 construct (Md-dnG1) as adjunctive intervention for superficial corneal opacity/corneal scarring. Hum Gene Ther. 2003;14(3):306-9.

Tolcher, et al. A randomized phase II and pharmacokinetic study of the antisense oligonucleotides ISIS 3521 and ISIS 5132 in patients with hormone-refractory prostate cancer. Clinical Cancer Research. 2002; 8: 2530-2535.

Tomasoni, et al. Gene therapy: how to target the kidney. Promises and pitfalls. current Gene Therapy. 2004; 4(1):115-122.

Valsesia-Wittmann, et al. Improvement of retroviral retargeting by using amino acid spacers between an additional binding domain and the N terminus of Moloney murine leukemia virus SU. J. Virol. 1996; 70(3): 2059-2064.

Williams, et al. Identification of a novel cyclin-like protein in human tumor cells. Journal of Biological Chemistry. 1993; 268:8871-8880.

Wong, et al. Bone Marrow Transplantation Experimentation. Abstract 1001. Dec. 1994.

Xie, et al. Elements within the first 17 amino acids of human osteonectin are responsible for binding to type V collagen. J. Biol. Chem. 1996; 271(14):8121-8125.

Xu, et al. Long term inhibition of neointima formation in balloon-injured rat arteries by intraluminal instillation of a matrix-targeted retroviral vector bearing a cytocidal mutant cyclin G1 construct. Int J Mol Med. 2001;8(1):19-30.

Yang, X. Imaging of vascular gene therapy. Radiology. 2003; 228:36-49.

Smirnov, et al. Carrier-directed targeting of liposomes and erythrocytes to denuded areas of vessel wall. Proc Natl Acad Sci U S A. Sep. 1986;83(17):6603-7.

Takagi, et al. A collagen/gelatin-binding decapeptide derived from bovine propolypeptide of von Willebrand factor. Biochemistry. Sep, 15, 1992;31(36):8530-4.

Cosset, et al. Retroviral retargeting by envelopes expressing an N-terminal binding domain J Virol. Oct. 1995;69(10):6314-22.

Ito, et al. Quaternary structure-dependent idiotope and antigen binding of a monoclonal antibody specific for conformational epitope on type II collagen. Cell Mol Life Sci. Jan. 1997;53(1):51-60.

Russell, et al. Retroviral vectors displaying functional antibody fragments. Nucleic Acids Res. Mar. 11, 1993;21(5):1081-5.

Somia, et al. Generation of targeted retroviral vectors by using single-chain variable fragment: an approach to in vivo gene delivery. Proc Natl Acad Sci U S A. Aug. 1, 1995;92(16):7570-4.

Tuan, et al. Engineering, expression and renaturation of targeted TGF-beta fusion proteins. Connect Tissue Res. 1996;34(1):1-9.

European search report dated Feb. 6, 2009 for Application No. 8004101.5.

European search report dated Apr. 12, 2001 for Application No. 98914585.9.

European search report dated Nov. 10, 2008 for Application No. 8004101.5.

International search report dated Jul. 27, 1998 for PCT Application No. US98/06936.

\* cited by examiner

TRANSGENE DELIVERING RETROVIRUS TARGETING COLLAGEN EXPOSED AT SITE OF TISSUE INJURY

CROSS-REFERENCE

This application is a continuation of application Ser. No. 11/014,629, filed on Dec. 15, 2004, now U.S. Pat. No. 7,347,998 which is a continuation of application Ser. No. 09/904,923, filed on Jul. 13, 2001, now U.S. Pat. No. 6,864,082, which is a continuation of U.S. application Ser. No. 08/837,223, filed on Apr. 10, 1997, now abandoned, which are incorporated herein by reference in their entirety.

This invention relates to a protein or polypeptide which is a modified viral surface protein or modified viral-derived surface protein, such as, for example, a modified retroviral envelope polypeptide, a modified adenoviral hexo protein, a modified adenoviral fiber protein, adeno-associated virus naked protein coat, or a modified Herpes Virus envelope protein. This invention further relates to "targeted" viral or non-viral vector particles, including retroviral vector particles, adenoviral vector particles, adeno-associated virus vector particles, Herpes Virus vector particles, and pseudotyped viruses, and to non-viral vectors that contain a viral protein as part of a virosome or other proteoliposomal gene transfer vector. More particularly, this invention relates to viral and non-viral vector particles, including retroviral vector particles, adenoviral vector particles, adeno-associated virus vector particles, Herpes Virus vector particles, pseudotyped viruses, and non-viral vectors having a modified, or chimeric viral surface protein, such as, for example, a chimeric viral envelope polypeptide, wherein such modified viral surface protein, such as a modified viral envelope polypeptide, includes a targeting polypeptide including a binding region which binds to an extracellular matrix component. The targeting polypeptide may be placed between two consecutive amino acid residues of the viral surface protein, or may replace amino acid residues which have been removed from the viral surface protein. The term "polypeptide" as used herein means a polymer of amino acids and does not refer to any particular length of polymer. Such term also includes post-translationally modified polypeptides or proteins (e.g., glycosylated, acetylated, phosphorylated, etc.).

BACKGROUND OF THE INVENTION

Retroviral vector particles are useful agents for introducing polynucleotides into cells, such as eukaryotic cells. The term "introducing" as used herein encompasses a variety of methods of transferring polynucleotides into a cell, such methods including transformation, transduction, transfection, and transinfection.

Retroviruses typically have three common open reading frames, gag, pol, and env, which encode the structural proteins, encode enzymes including reverse transcriptase, and encode envelope proteins, respectively. Typically, retroviral vector particles are produced by packaging cell lines that provide the necessary gag, pol, and env gene products in trans. (Miller, et al., *Human Gene Therapy*, Vol. 1, pgs. 5-14 (1990)). This approach results in the production of retroviral vector particles which transduce mammalian cells, but are incapable of further replication after they have integrated into the genome of the cell.

Thus, retroviral vector particles have been used for introducing polynucleotides into cells for gene therapy purposes. In one approach, cells are obtained from a patient, and retroviral vector particles are used to introduce a desired polynucleotide into the cells, and such modified cells are returned to the patient with the engineered cells for a therapeutic purpose. In another approach, retroviral vector particles may be administered to the patient in vivo, whereby the retroviral vector particles transduce cells of the patient in vivo.

While the initial applications of human gene therapy have been performed in accessible sites and in target cells that are manipulated readily ex vivo, it is anticipated that future gene therapy protocols will describe systemic delivery of recombinant vectors for a wide variety of cardiovascular and other diseases. (Ledley, et al., *Molecular Genetics and Gene Therapy of Cardiovascular Disease*, Mockrin, ed., Marcel Dekker, Inc., New York, pgs. 467-485 (1995); Nabel, *Circulation*, Vol. 91, pgs. 541-548 (1995)). Development of the technologies associated with tissue targeting will expand greatly the scope of gene therapy in cardiovascular and other fields of medicine. The effectiveness of retroviral vectors for gene delivery to cardiovascular and other tissues is limited by the inefficiency of gene transfer into intact vascular endothelium, the inactivation of retroviral vectors in vivo, and by the inability to localize effective vector concentrations at remote physiological sites. Thus, the use of retroviral vectors in vivo for gene delivery to cardiovascular and other tissues depends upon effective viral titer, stability, tissue targeting, and the ability to transduce vascular cells. Presently, the targeted delivery of the therapeutic genes to impaired, diseased, or transplanted vasculature remains a major challenge in the development of gene therapy protocols for cardiovascular disease.

SUMMARY OF THE INVENTION

Targeting of retroviral vectors can be divided into four separate processes: (i) delivery of concentrated viral particles; (ii) docking of the virus to the target cell; (iii) internalization of the viral core; and (iv) expression of the desired transgene. (Salmons, et al., *Human Gene Therapy*, Vol. 4, pgs. 129-141 (1993)). In contrast to previous approaches for achieving tissue targeting by genetic engineering of the retroviral envelope protein to incorporate polypeptide ligands to cellular receptors (Kasahara, et al., *Science*, Vol. 266, pgs. 1373-1376 (1994); Valseria-Wittmann, et al., *J. Virol.*, Vol. 68, pgs. 4609-4619 (1994)) or single chain antibodies that recognize cell specific antigens (Russell, *Nucl. Acids Res.*, Vol. 21, pgs. 1081-1085 (1993); Cosset, et al., *J. Virol.*, Vol. 69, pgs. 6314-6322 (1995); Somia, et al., *Proc. Nat. Acad. Sci.*, Vol. 92, pgs. 7570-7574 (1995)), the present invention is directed to viral vectors, such as retroviral vectors, adenoviral vectors, adeno-associated virus vectors, Herpes Virus vectors, and pseudotyped viruses, as well as virosomes or proteoliposomes and other non-viral vectors which are designed to utilize the basic biology of wound healing to concentrate the delivery of therapeutic genes to sites of tissue injury. More particularly, the present invention is directed to viral and non-viral vector particles, such as, retroviral vector particles, adenoviral vector particles, adeno-associated viral particles, Herpes Virus particles, pseudotyped viruses, and non-viral vectors having a modified viral surface protein, wherein the viral surface protein, such as, for example, a viral envelope polypeptide, has been modified to include a targeting polypeptide which includes a binding region which binds to an extracellular matrix component, whereby the targeting of the viral or non-viral vectors to an extracellular matrix component improves the specificity and/or local concentration of the vectors. The term "extracellular matrix component", as used herein, means a molecule that occupies the extracellular spaces of tissues.

BRIEF DESCRIPTION OF THE DRAWINGS

The invention now will be described with respect to the drawings, wherein:

FIG. 3B shows selective binding of chimeric viruses to collagen matrices in microtiter wells;

DETAILED DESCRIPTION OF THE INVENTION

Figure 1A:
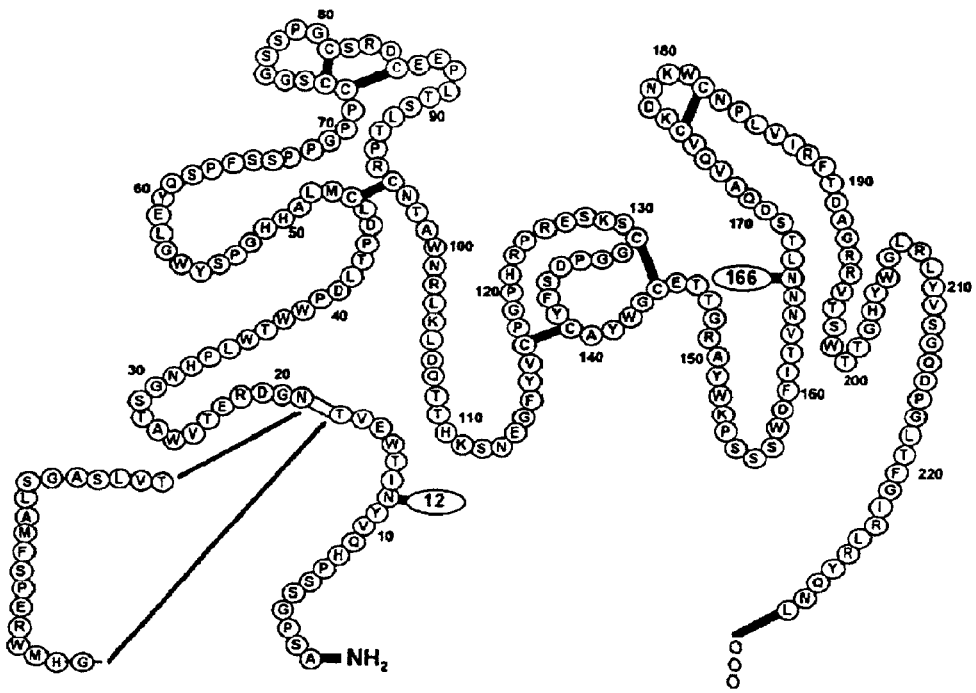
FIG. 1A is a schematic of the receptor binding region of ecotropic gp70 protein (SEQ ID NO:1), showing the insertion of a polypeptide including a collagen-binding domain between amino acid residues 18 and 19.

In accordance with an aspect of the present invention, there is provided a vector particle having a modified viral surface protein, such as, for example, a modified viral envelope polypeptide, for targeting the vector particle to an extracellular matrix component. The viral surface protein is modified to include a targeting polypeptide including a binding region which binds to an extracellular matrix component.

Vector particles which have a modified surface protein include any viral or non-viral vector particle which may be employed for gene transfer to cells in vivo, ex vivo, or in vitro, or for gene therapy. Such vector particles include, but are not limited to retroviral vector particles, adenoviral vector particles, adeno-associated virus particles, Herpes Virus particles, pseudotyped viruses, and non-viral vectors. The targeting polypeptide may be placed in any region of any viral surface protein. The targeting polypeptide, in one embodiment, may be placed between two consecutive amino acid residues of a viral surface protein. Alternatively, amino acid residues of a viral surface protein are removed and replaced with the targeting polypeptide.

Viral surface proteins which may be modified include, but are not limited to, retroviral envelope proteins, adenoviral hexon proteins, adenoviral fiber proteins, adeno-associated virus naked protein coats, and Herpes Virus envelope proteins. It is to be understood, however, that the scope of the present invention is not to be limited to any particular modified viral surface protein.

In one embodiment, the vector particle is a viral vector particle, and in one embodiment, the viral vector particle is a retroviral vector particle. Any portion of the retroviral envelope may be modified to include the targeting polypeptide. In one embodiment, the receptor binding region of the retroviral envelope is modified to include the targeting polypeptide.

In one embodiment, the targeting polypeptide is inserted between two consecutively numbered amino acid residues of the native (i.e., unmodified) receptor binding region of the retroviral envelope. In another embodiment, amino acid residues of the receptor binding region may be removed and replaced with the targeting polypeptide. In one embodiment, prior to modification, the receptor binding region has the sequence (SEQ ID NO:1), which is the receptor binding region of an ecotropic retroviral envelope. In the modified envelope polypeptide, the targeting polypeptide is inserted between amino acid residues 18 and 19 of (SEQ ID NO:1). In another embodiment, in the modified envelope polypeptide, the targeting polypeptide is inserted between amino acid residues 6 and 7 of (SEQ ID NO:1).

The polypeptide (SEQ ID NO:1) is a portion of a protein known as gp70, which is included in the ecotropic envelope of Moloney Murine Leukemia Virus. In general, gp70 protein includes the following regions: (i) the secretory signal or "leader" sequence; (ii) the receptor binding region; (iii) the hinge region; and (iv) the body portion. (SEQ ID NO:1) is the receptor binding region of the ecotropic envelope of Moloney Murine Leukemia Virus. Applicants have found that retroviruses can be made "targetable" to an extracellular matrix component if the receptor binding region is modified such that the receptor binding region includes a polypeptide which binds to an extracellular matrix component.

As an alternative to modifying the receptor binding region, or in addition to the modified receptor binding region, the retroviral particles may have modifications in other regions of the envelope protein such that other regions of the envelope may include the targeting polypeptide, such as, for example, the secretory signal or "leader" sequence, the hinge region, or the body portion. Such modifications may include deletions or substitutions of amino acid residues in the retroviral envelope wherein amino acid residues from regions other than the receptor binding region of the envelope are removed and replaced with the targeting polypeptide, or the targeting polypeptide is placed between consecutively numbered amino acid residues of regions other than the receptor binding region of the viral envelope.

In another alternative embodiment, the retroviral envelope, prior to modification thereof to include the targeting polypeptide which binds to the extracellular matrix component, may be an envelope which includes regions of different tropisms. For example, the retroviral envelope may be a Moloney Murine Leukemia Virus envelope which includes a gp70 protein having an ecotropic portion and an amphotropic and/or xenotropic portion.

In general, the targeting polypeptide includes a binding region which binds to an extracellular matrix component, including, but not limited to, collagen (including collagen Type I and collagen Type IV), laminin, fibronectin, elastin, glycosaminoglycans, proteoglycans, and sequences which bind to fibronectin, such as arginine-glycine-aspartic acid, or RGD, sequences. Binding regions which may be included in the targeting polypeptide include, but are not limited to, polypeptide domains which are functional domains within von Willebrand Factor or derivatives thereof, wherein such polypeptide domains bind to collagen. In one embodiment, the binding region is a polypeptide having the following structural formula: Trp-Arg-Glu-Pro-Ser-Phe-Met-Ala-Leu-Ser. (SEQ ID NO:3).

Other binding regions which may be included in the viral envelope, include but are not limited to, the arginine-glycine-aspartic acid, or RGD, sequence, which binds fibronectin, and a polypeptide having the sequence Gly-Gly-Trp-Ser-His-Trp (SEQ ID NO: 4), which also binds to fibronectin.

In addition to the binding region, the targeting polypeptide may further include linker sequences of one or more amino acid residues, placed at the N-terminal and/or C-terminal of the binding region, whereby such linkers increase rotational flexibility and/or minimize steric hindrance of the modified envelope polypeptide.

It is to be understood, however, that the scope of the present invention is not to be limited to any specific targeting polypeptide or binding region.

In accordance with another aspect of the present invention, there is provided a modified polynucleotide encoding a modified viral surface protein for targeting a vector to an extracellular matrix component. Such polynucleotide includes a polynucleotide encoding a targeting polypeptide including a binding region which binds to an extracellular matrix component. The vector and modified viral surface protein may be selected from those hereinabove described.

In one embodiment, the vector is a retroviral vector, and the modified viral surface protein is a modified retroviral envelope polypeptide. The envelope polypeptide includes a receptor binding region. In one embodiment, in the modified polynucleotide, the polynucleotide encoding the receptor binding region is modified to include a polynucleotide encoding a targeting polypeptide including a binding region which binds to an extracellular matrix component.

In one embodiment prior to modification, the polynucleotide encoding the receptor binding region encodes a receptor binding region having the sequence (SEQ ID NO:1). In the modified polynucleotide, the polynucleotide encoding the targeting polypeptide is inserted between the codon encoding amino acid residue 18 and the codon encoding amino acid residue 19 of (SEQ ID NO:1). In another embodiment, in the modified polynucleotide, the polynucleotide encoding the targeting polypeptide is inserted between the codon encoding amino acid residue 6 and the codon encoding amino acid residue 7 of (SEQ ID NO:1). The receptor binding region having the sequence (SEQ ID NO:1) is encoded by the polynucleotide having (SEQ ID NO:2) or a derivative or analogue thereof.

The term "derivative or analogue thereof" as used herein means that the polynucleotide encoding the polypeptide (SEQ ID NO:1) may have a sequence different from the polynucleotide (SEQ ID NO:2), yet encode the same polypeptide. Such differences in polynucleotide sequences may, for example, be due to the degeneration of the genetic code. It is also contemplated within the scope of the present invention that, prior to the modification of (SEQ ID NO:2) with a polynucleotide encoding a targeting polypeptide, (SEQ ID NO:2) may be modified such that one or more codons are changed such that the coders modify different amino acid residues than the unmodified sequences. Such modifications may facilitate the insertion of the polynucleotide encoding the targeting polypeptide.

The above polynucleotides may be constructed by genetic engineering techniques known to those skilled in the art. For example, a first expression plasmid may be constructed which includes a polynucleotide encoding the unmodified envelope. The plasmid then is engineered such that a polynucleotide encoding the targeting polypeptide is inserted between two codons encoding consecutively numbered amino acid residues of the unmodified envelope, or is engineered such that a polynucleotide encoding a portion of the unmodified envelope is removed, whereby such portion way be replaced with a polynucleotide encoding the targeting polypeptide. The polynucleotide encoding the targeting polypeptide may be contained in a second expression plasmid or may exist as a naked polynucleotide sequence. The polynucleotide encoding the targeting polypeptide or the plasmid containing such polynucleotide is cut at appropriate restriction enzyme sites and cloned into the first expression plasmid which also has been cut at appropriate restriction enzyme sites. The resulting expression plasmid thus includes a polynucleotide encoding the modified envelope protein. Such polynucleotide then may be cloned out of the expression plasmid, and into a retroviral plasmid vector. The resulting retroviral plasmid vector, which includes the polynucleotide encoding the modified envelope protein, and which also may include a polynucleotide encoding a heterologous protein or peptide, is transfected into an appropriate packaging cell line to form a producer cell line for generating retroviral vector particles including the modified envelope protein. Alternatively, a naked polynucleotide sequence encoding the modified envelope protein is transfected into a "pre-packaging" cell line including nucleic acid sequences encoding the gag and pol proteins, thereby forming a packaging cell line, or is transfected into a packaging cell line including nucleic acid sequences encoding the gag, pol, and wild-type (i.e., unmodified) env proteins, thereby forming a packaging cell line including nucleic acid sequences encoding wild-type env protein and the modified envelope protein. Such packaging cells then may be transfected with a retroviral plasmid vector, which may include a nucleic acid sequence encoding a heterologous protein or peptide, thereby forming a producer cell line for generating retroviral vector particles including the modified envelope protein. Such a polynucleotide thus may be contained in the above-mentioned retroviral vector particle, or in a producer cell for generating the above-mentioned retroviral vector particle.

The term "polynucleotide" as used herein means a polymeric form(s) of nucleotide(s) of any length, and includes ribonucleotides and/or deoxyribonucleotides. Such term also includes single- and double-stranded DNA, as well as single- and double-stranded RNA. The term also includes modified polynucleotides such as methylated or capped polynucleotides.

In a preferred embodiment, the vector particle having a modified envelope in accordance with the invention includes a polynucleotide encoding a heterologous polypeptide which is to be expressed in a desired cell. The heterologous polypeptide may, in one embodiment, be a therapeutic agent. The term "therapeutic" is used in a generic sense and includes treating agents, prophylactic agents, and replacement agents.

Examples of therapeutic agents include, but are not limited to, cell cycle control agents, agents which inhibit cyclin proteins, such as antisense polynucleotides to the cyclin G1 and cyclin D1 genes, growth factors such as, for example, epidermal growth factor (EGF), vascular endothelial growth factor (VEGF), erythropoietin, G-CSF, GM-CSF, TGF-α, TGF-β, and fibroblast growth factor, cytokines, including, but not limited to, Interleukins 1 through 13 and tumor necrosis factors, anticoagulants, anti-platelet agents, anti-inflammatory agents, tumor suppressor proteins, clotting factors, including Factor VIII and Factor IX, protein S, protein C, antithrombin III, von Willebrand Factor, cystic fibrosis transmembrane conductance regulator (CFTR), and negative selective markers such as Herpes Simplex Virus thymidine kinase.

It is to be understood, however, that the scope of the present invention is not to be limited to any particular therapeutic agent.

The polynucleotide encoding the therapeutic agent is under the control of a suitable promoter. Suitable promoters which may be employed include, but are not limited to, the retroviral LTR; the SV40 promoter; the cytomegalovirus (CKV) promoter; the Rous Sarcoma Virus (RSV) promoter; the histone promoter; the polIII promoter, the β-actin promoter; inducible promoters, such as the MMTV promoter, the metallothionein promoter; heat shock promoters; adenovirus promoters; the albumin promoter; the ApoAI promoter; B19 parvovirus promoters; human globin promoters; viral thymidine kinase promoters, such as the Herpes Simplex Virus thymidine kinase promoter; retroviral LTRs; human growth hormone promoters, and the MxIFN inducible promoter. The promoter also may be the native promoter which controls the polynucleotide encoding the therapeutic agent. It is to be understood, however, that the scope of the present invention is not to be limited to specific foreign genes or promoters.

The polynucleotides encoding the modified envelope polypeptide and the therapeutic agent may be placed into an appropriate vector by genetic engineering techniques known to those skilled in the art. When the modified vector is a retroviral vector particle, the polynucleotides encoding the modified envelope polypeptide and the therapeutic agent are placed into an appropriate retroviral plasmid vector.

In one embodiment, the retroviral plasmid vector may be derived from Moloney Murine Leukemia Virus and is of the LN series of vectors, such as those hereinabove mentioned, and described further in Bender, et al., *J. Virol.*, Vol. 61, pgs. 1639-1649 (1987) and Miller, et al., *Biotechniques*, Vol. 7, pgs 980-990 (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral plasmid vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral plasmid vector includes each of these cloning sites. Such vectors are further described in U.S. patent application Ser. No. 08/340,805, filed Nov. 17, 1994, and in PCT Application No. W091/10728, published Jul. 25, 1991, and incorporated herein by reference in their entireties.

When a retroviral plasmid vector including such cloning sites is employed, there may also be provided a shuttle cloning vector which includes at least two cloning sites which are compatible with at least two cloning sites selected from the group consisting of NotI, SnaBI, SalI, and XhoI located on the retroviral plasmid vector. The shuttle cloning vector also includes at least one desired polynucleotide encoding a therapeutic agent which is capable of being transferred from the shuttle cloning vector to the retroviral plasmid vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The retroviral plasmid vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

In one embodiment, the retroviral plasmid vector, which includes a polynucleotide encoding the modified envelope and a polynucleotide encoding a therapeutic agent, is employed to transduce a packaging cell line to form a producer cell line, which will generate infectious retroviral vector particles. In one embodiment, the packaging cell line is a "pre-packaging" cell line which includes polynucleotides encoding the gag and pol retroviral proteins, but not the envelope, or env, protein. Examples of such "pre-packaging" cell lines include, but are not limited to, GP8 cells, GPL cells, and GPNZ cells as described in Morgan, et al., *J. Virol.*, Vol. 67, No. 8, pgs. 4712-4721 (August 1993). Such cell lines, upon transduction with the retroviral plasmid vector, generates infectious retroviral particles including the modified, or chimeric, envelope and a polynucleotide encoding the therapeutic agent.

In another embodiment, a retroviral plasmid vector which includes a polynucleotide encoding a modified polynucleotide encoding a modified envelope polypeptide in accordance with the invention and a polynucleotide encoding a therapeutic agent is used to transduce a packaging cell line including nucleic acid sequences encoding the gag, pol, and wild-type (i.e., unmodified) env retroviral proteins. Examples of such packaging cell lines include, but are not limited to, the PE501, PA317 (ATCC No. CRL 9078), ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5-14 (1990), which is incorporated herein by reference in its entirety. The vector may transduce the packaging cells through any means known in the art. Such means include, but are not limited to, electroporation, and use of liposomes, such as hereinabove described, and $CaPO_4$ precipitation. Such producer cells generate infectious retroviral vector particles which include the modified envelope, the wild-type retroviral envelope, a polynucleotide encoding the modified, or chimeric, envelope, and a polynucleotide encoding a therapeutic agent.

In another embodiment, there is provided a packaging cell which includes a nucleic acid sequence encoding a modified chimeric envelope in accordance with the invention, and which may further include nucleic acid sequences encoding the gag and pol proteins. A producer cell for generating viral particles which includes a modified envelope in accordance with the invention is produced by introducing into such packaging cell either a retroviral vector particle or a retroviral plasmid vector, in each case including a polynucleotide encoding a therapeutic agent. The producer cell line thus generates infectious retroviral particles including the modified chimeric envelope and the polynucleotide encoding the therapeutic agent.

The vector particles, which include the modified viral surface protein, such as, for example, a modified retroviral envelope, and a polynucleotide encoding a therapeutic agent, may be administered to a host in an amount effective to produce a therapeutic effect in the host. The host may be a mammalian host, which may be a human or non-human primate host. The vector particles, upon administration to the host, become concentrated at a site of an exposed matrix component, such as, for example, collagen (including Type I collagen and Type IV collagen), laminin, fibronectin, elastin, glycosaminoglycans, proleoglycans or an RGD sequence, whereby the viral vector particles infect or transduce the cells at such site of the exposed extracellular matrix component, and the infected or transduced cells express the therapeutic agent in vivo. The exact dosage of vector particles which may be administered is dependent upon a variety of factors, including the age, sex, and weight of the patient, the cells which are to be transduced, the therapeutic agent which is to be administered, and the severity of the disorder to be treated.

The vector particles may be administered systemically, such as, for example, by intravenous, intracolonic, intratracheal, intraperitoneal, intranasal, intravascular, intrathecal, intraarterial, intracranial, intramarrow, intrapleural, intradermal, subcutaneous, intramuscular, intraocular, intraosseous and/or intrasynovial administration. The vector particles also may be administered topically.

Cells which may be infected or transduced with the vector particles of the present invention include, but are not limited to, endothelial cells, tumor cells, chondrocytes, fibroblasts and fibroelastic cells of connective tissues; osteocytes and osteoblasts in bone; endothelial and smooth muscle cells of the vasculature; epithelial and subepithelial cells of the gastrointestinal and respiratory tracts; vascular cells, connective tissue cells, and hepatocytes of a fibrotic liver, and the reparative mononuclear and granulocytic infiltrates of inflamed tissues.

Diseases or disorders which may be treated with the vector particles of the present invention include, but are not limited to, those associated with an exposed extracellular matrix component. Such diseases or disorders include, but are not limited to, cardiovascular diseases; cirrhosis of the liver; and connective tissue disorders (including those associated with ligaments, tendons, and cartilage), and vascular disorders associated with the exposition of collagen. The vector particles may be used to deliver therapeutic genes to restore endothelial cell function and to combat thrombosis, in addition to limiting the proliferative and fibrotic responses associated with neointima formation. The vector particles also may be employed in treating vascular lesions; ulcerative lesions; areas of inflammation; sites of laser injury, such as the eye, for example; sites of surgery; arthritic joints; scars; and keloids. The vector particles also may be employed in would healing.

The vector particles also may be employed in the treatment of tumors, including malignant and non-malignant tumors. Although Applicants do not intend to be limited to any theoretical reasoning, tumors, when invading normal tissues or organs, secrete enzymes such as collagenases or metalloproteinases which provide for the exposition of extracellular matrix components. By targeting vector particles to such exposed extracellular matrix components, the vector particles become concentrated at the exposed matrix-components which are adjacent the tumor, whereby the vector particles then infect the tumor cells. Such tumors include, but are not limited to, carcinomas; sarcomas, including chondrosarcoma, osteosarcoma, and fibrosarcoma; and brain tumors. For example, a vector particle, such as a retroviral vector particle, including a modified envelope protein, including a targeting polypeptide which binds to an extracellular matrix component located at a tumor site, and a polynucleotide encoding a negative selective marker or "suicide" gene, such as, for example, the Herpes Simplex Virus thymidine kinase (TX) gene, may be administered to a patient, whereby the vector particles transduce the tumor cells. After the tumor cells are transduced with the vector particles, an interaction agent, such as gancyclovir or acyclovir, is administered to the patient, whereby the transduced tumor cells are killed.

Other polynucleotides encoding anti-tumor agents which may be contained in the vector particles include, but are not limited to, polynucleotides encoding cell cycle control agents, polynucleotides (such as, for example, antisense polynucleotides) which bind to polynucleotides encoding cyclin G1 or cyclin D1, tumor suppressor proteins, anti-angiogenic factors, such as, for example, endothelial monocyte activating polypeptide-2 (RMAP-2), cytokines and growth factors, which include those cytokines and growth factors hereinabove described. The vector particles including such polynucleotides are administered to a patient, whereby the vector particles bind to an extracellular matrix component located at a tumor site, and then transduce the tumor cells. Growth of the tumor cells is inhibited, suppressed, or destroyed upon expression of the anti-tumor agent by the transduced tumor cells.

It is to be understood that the present invention is not to be limited to the treatment of any particular disease or disorder.

The vector particles, which include the modified viral surface protein and a polynucleotide encoding a therapeutic agent, may be administered to an animal in vivo as part of an animal model for the study of the effectiveness of a gene therapy treatment. The vector particles may be administered in varying doses to different animals of the same species, whereby the vector particles will bind to an extracellular matrix component in the animal. The animals then are evaluated for the expression of the desired therapeutic agent in vivo in the animal. From the data obtained from such evaluations, one may determine the amount of vector particles to be administered to a human patient.

The vector particles, which include the modified viral surface protein and a polynucleotide encoding a therapeutic agent, may be concentrated from dilute vector stocks in vitro by contacting a dilute vector stock with an extracellular matrix component to which the modified viral surface protein will bind. Such binding enables one to obtain a concentrated stock of the vector particles.

In addition, the modified viral surface proteins of the present invention may be employed to form proteoliposomes; i.e., the modified viral surface protein forms a portion of the liposome wall. Such proteoliposomes may be employed for gene transfer or for drug delivery to cells located at a site of an exposed extracellular matrix component.

EXAMPLES

The invention now will be described with respect to the following examples; however, the scope of the present invention is not intended to be limited thereby.

Example 1

Figure 1B:
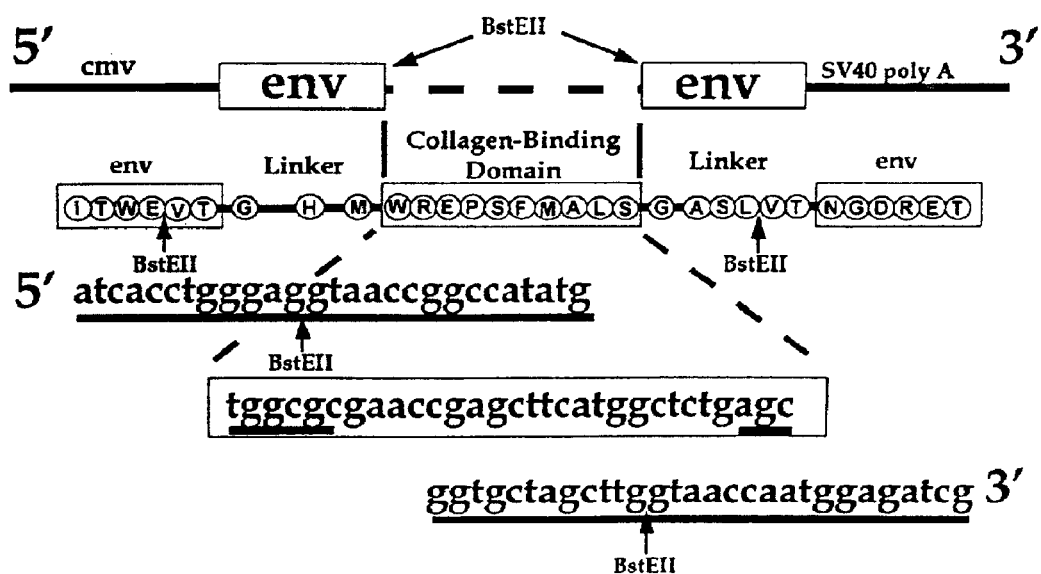
FIG. 1B is a schematic of the envelope structure and cloning strategy employed to insert a collagen-binding polypeptide flanked by linker amino acid residues into the unique BstEII site within the N-terminal region of ecotropic gp70 protein. Figure discloses SEQ ID NOS 12-14, bases 1-27 of 8, 7 and 15, respectively, in order of appearance.

Cee+ is a CMV-env expression vector constructed by digesting CEE (Morgan, et al., *J. Virol.*, Vol. 67, No. 8, pgs. 4712-4721 (August 1993)) with HindIII and NotI, filling in the NotI site with a Klenow fragment, and ligating the CMV-env cassette into pBluescript II SK+ (Stratagene, La. Jolla, Calif.) digested with SmaI and HindIII. PCR and recombinant DNA technologies then were employed to make the construct ECE-CEE+, which includes a polynucleotide encoding a chimeric Moloney Mitrine Leukemia Virus based gp70 envelope protein that incorporates a high-affinity collagen binding domain within its primary structure (FIG. 1A). The modified collagen binding domain was derived from a functional domain within von Willebrand Factor involved in the recognition of exposed vascular collagen sequences. (Takagi, et al., *Biochemistry*, Vol. 32, pgs. 8530-8534 (1992); Tuan, et al., *Conn. Tiss. Res.*, Vol. 34, pgs. 1-9 (1996)). ECB-CEE+ incorporates a polypeptide which includes the collagen binding decapeptide WREPSFMALS. This construct was designed specifically for targeting a retrovirus to collagen exposed by injury, inflammation, disease, or reparative surgical procedures. The cysteine residue within the original von Willebrand Factor sequence was replaced conservatively by a methionine, in order that the collagen binding domain would not interfere with the elaborate disulfide bond formation required for the folding and/or renaturation of gp70. Flanking linkers also were designed to include glycine residues to increase rotational flexibility and to minimize steric hindrances, while a histidine residue was included to promote an external conformation of the collagen binding domain. The complete 19 amino acid polypeptide insert, which includes the collagen binding decapeptide, is shown in FIG. 1A and FIG. 1B.

The construct ECBT-CEE+ includes the same components as ECB-CEE+ as well as a six amino acid residue putative thrombin cleavage site, which has the sequence LVPRGS (SEQ ID NO: 5), between the collagen-binding domain and the remainder of the envelope protein.

ECB-CEE+ and ECBT-CEE+ were constructed using PCR and recombinant DNA technologies as mentioned above. The collagen binding decapeptide WREPSFMALS (SEQ ID NO: 6) is encoded by the following polynucleotide: TGG CGC GAA CCG AGC TTC ATG GCT CTG AGC (SEQ ID NO: 7). The following PCR primers in making ECB-CEE+ were employed.

Sense (CBD-S1):5'-ATC ACC TGG GAG GTA ACC GGC CAT ATG TGG CGC-3' (SEQ ID NO: 8)

Antisense (CBD-aS1):5'-CG ATC TCC ATT GGT TAC CAA GCT AGC ACC GCT-3' (SEQ ID NO: 9)

CBD-S1 also was employed in making ECBT-CEE+, along with the following antisense primer CBDT-aS2:

5'-CG ATC TCC ATT GGT TAC CAA GCT GCC GCG CGG CAC CAG ACC GCT CAG AGC-3' (SEQ ID NO: 10)

Collagen binding domains with proper linkers were amplified by PCR using the primers CBDS1 and CBDaS1 or CBDS1 and CDaS2, respectively (94° C. 1 min, 55° C. 10 min, 72° C. 10 min., 35 cycles). The PCR bands then were digested with BstBII. Cee+ was digested with BstEII, followed by dephosphorylation of the linearized Cee+ vector. The digested PCR bands were ligated to the linearized Cee+ vector to form ECB-CEE+ and ECBT-CEE+. The proper orientations of the cDW constructs were confirmed by sequence analysis.

Figure 2A:
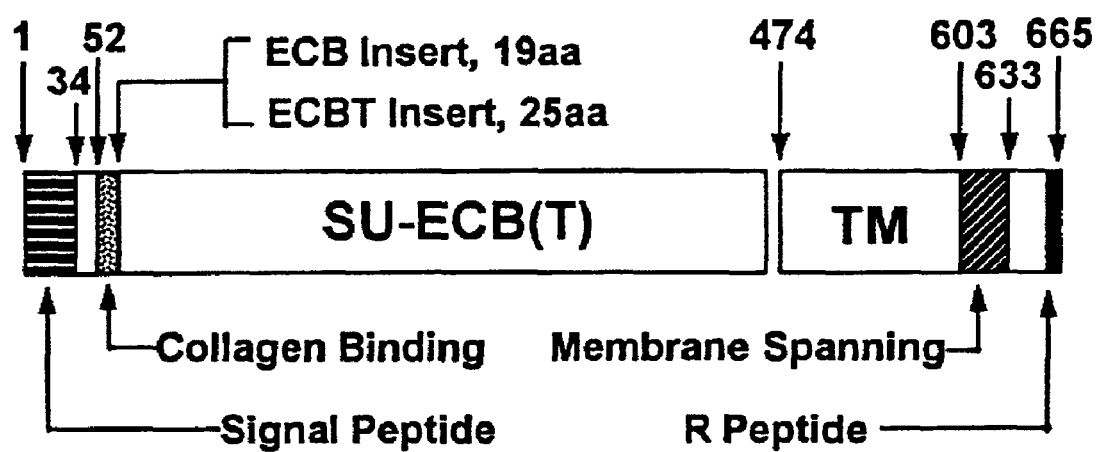
FIG. 2A is a schematic diagram of the Moloney Murine Leukemia Virus envelope protein identifying the surface (SU) and transmembrane (TM) polypeptides, as well as the signal peptide, auxiliary collagen-binding domain, membrane spanning and R peptide regions.

ECB-CEE+ was cut with NheI and EcoRI, and an NheI/EcoRI fragment including a polynucleotide encoding a modified ecotropic retroviral envelope was ligated to NheI and EcoRI digested plasmid pET28 (Tuan, et al. *Conn. Tiss. Res.*, Vol. 1, pgs. 1-9 (1996)) to form pET28SU-ECB-CEE+. Plasmid pET28SU-ECB-CEE+ includes a polynucleotide encoding a chimeric fusion protein containing a contiguous series of functional domains-a His×6 purification tag (SEQ ID NO: 11) and a von WIllebrand Factor derived collagen binding domain within the envelope structure followed by the mature surface (SU) region of MoMuLV env polypeptide, gp70, comprising amino acid residues 34 to 474, excluding the leader sequence. (FIG. 2A). As shown in FIG. 2A, amino acid residues 1 to 33 are the leader sequence. Amino acid residue 34 of FIG. 2A corresponds to amino acid residue 1 in FIG. 1A and (SEQ ID NO:1). The ECB and ECB(T) inserts each begin at amino acid residue 52.

Figure 2B:
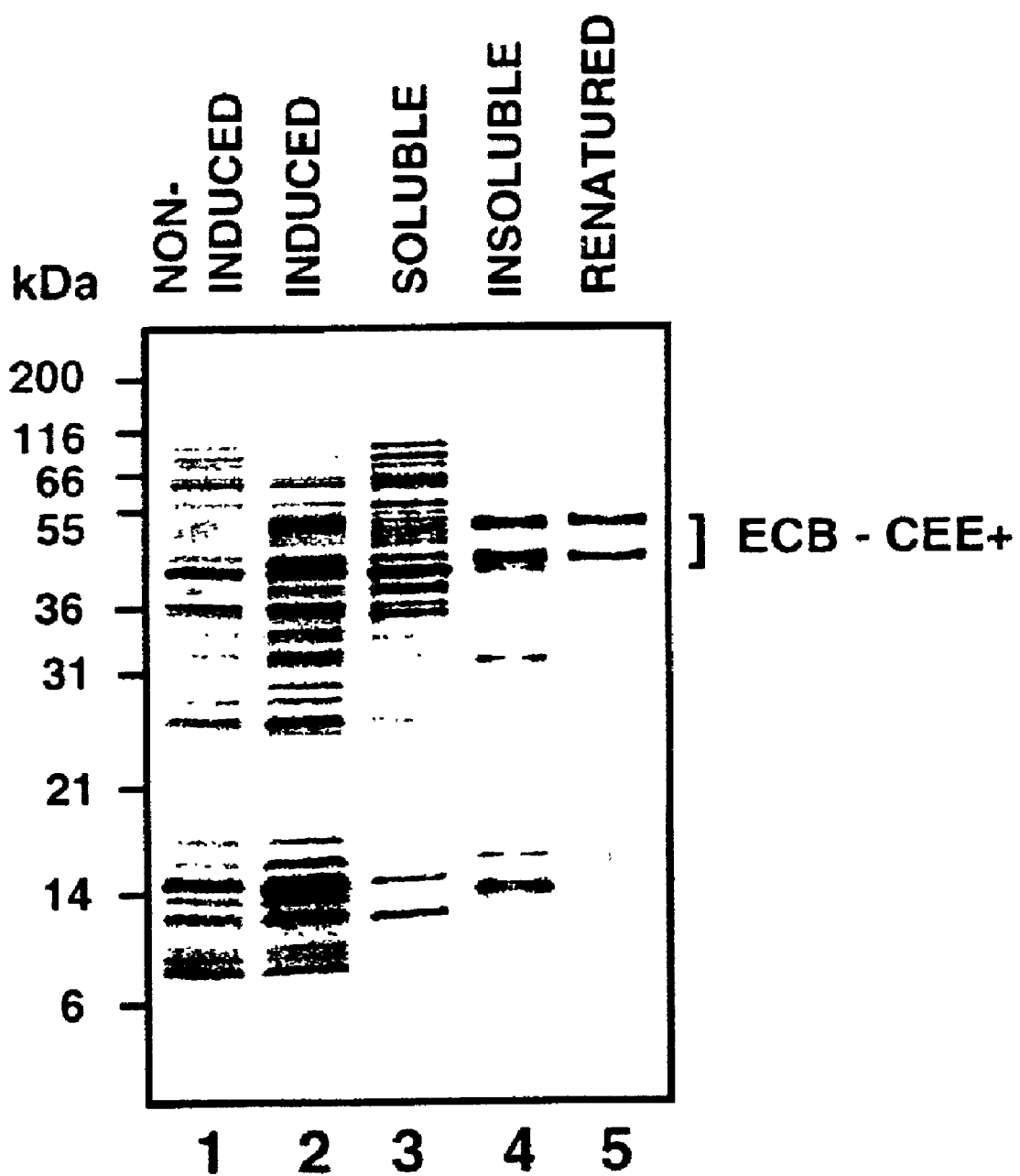
FIG. 2B shows an SDS-PAGB demonstrating the expression, purification, and renaturation of a chimeric envelope protein including a collagen-binding domain.

Plasmid pET28SU-ECB-CEE+ was transformed into the BL21 (DE 3) strain of *E. coli*, and high level expression of the recombinant proteins was induced in the presence of 1 mM IPTG for 4 hours at 37° C. The induced recombinant fusion protein was isolated from bacterial inclusion bodies, solubilized in 8M urea purified under denaturing conditions by metal (nickel) chelate chromatography (Qiagen), renatured by slow dilution (1:5) into Redox buffer (20 mM Tris HCl, pH 8.0, 250 mM NaCl, 0.05% NP 40, 2 mM reduced glutathione, and 0.2 M oxidized glutathione), and refolded for 16 hours at 4° C., followed by dialysis in protracted steps into 20 mM Tris HCl, pH 5.0, 250 mN NaCl, clarified by centrifugation at 10,000×g, and stored at −70° C. until used. SDS-PAGE which demonstrates the expression, purification, and renaturation of the recombinant protein, is shown in FIG. 2B.

Figure 2C:
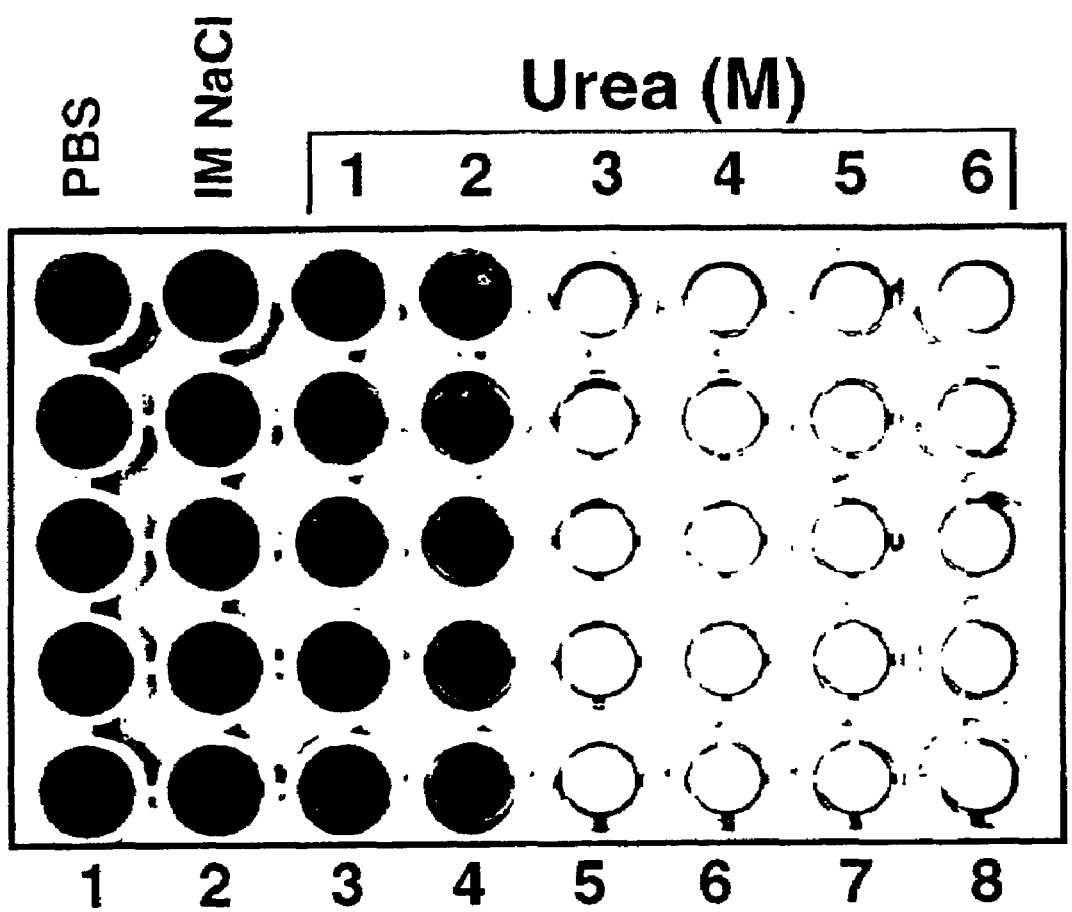
FIG. 2C shows the binding of the renatured recombinant choleric envelope protein in collagen-coated microtiter wells.

Binding of the recombinant protein to collagen was determined as follows:

Approximately 1 μg of the protein then was applied to collagen-coated microtiter plates and allowed to bind for 20 minutes followed by washing. The plates were incubated for 4 hours at room temperature at a primary antibody dilution of 1:1,000. A biotinylated goat antibody to rat IgG then was applied, followed by a strepavidin-horseradish peroxidase conjugate. Diaminobenzidine (DAB) was used as a chrogen followed by nickel chloride enhancement for microtiter plates. It also was shown that the renatured chimeric fusion protein bound to collagen matrices with high affinity, was not washed away by PBS (Lane 1), 1 M NaCl (Lane 2), or 2M urea, and required at least 3M urea to release the collagen-bound protein into solution (FIG. 2C).

Figure 3A:
FIG. 3A shows mock transfected (control) GPL cells that exhibit no positive staining for gp70 env protein.
Figure 3B:
FIG. 3B shows GPL cells transfected with CEE+, which expresses wild-type gp70.
Figure 3C:
FIG. 3C shows GPL cells transfected with chimeric ECB-CEE+ plasmid DNA.
Figure 3D:
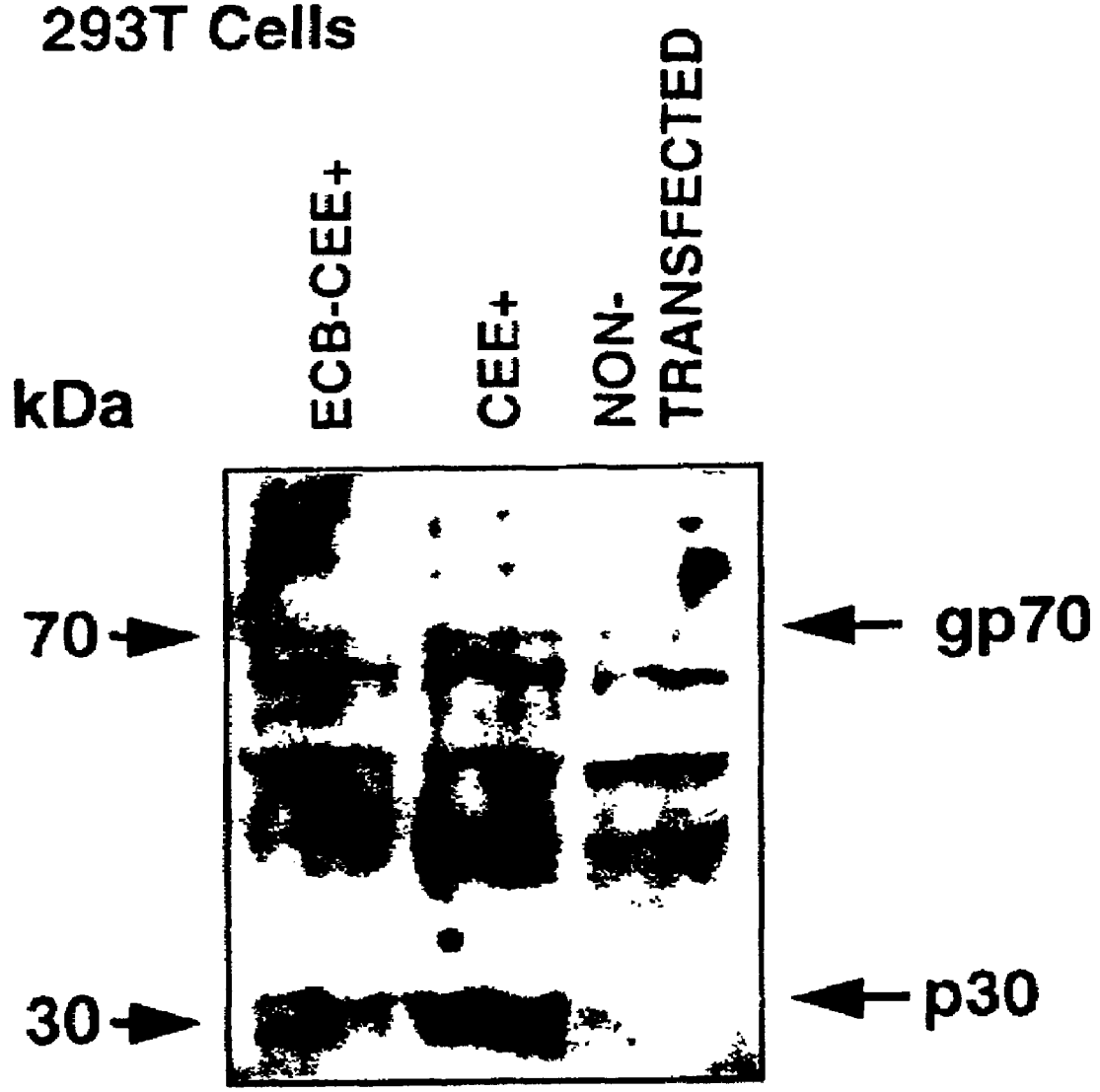
FIG. 3D is a Western Blot showing co-migration of the chimeric ECB-CEE+ env protein with wild-type CBR+ env protein, as well as co-migration of the gag proteins in the 30 kda region.
Figure 3E:
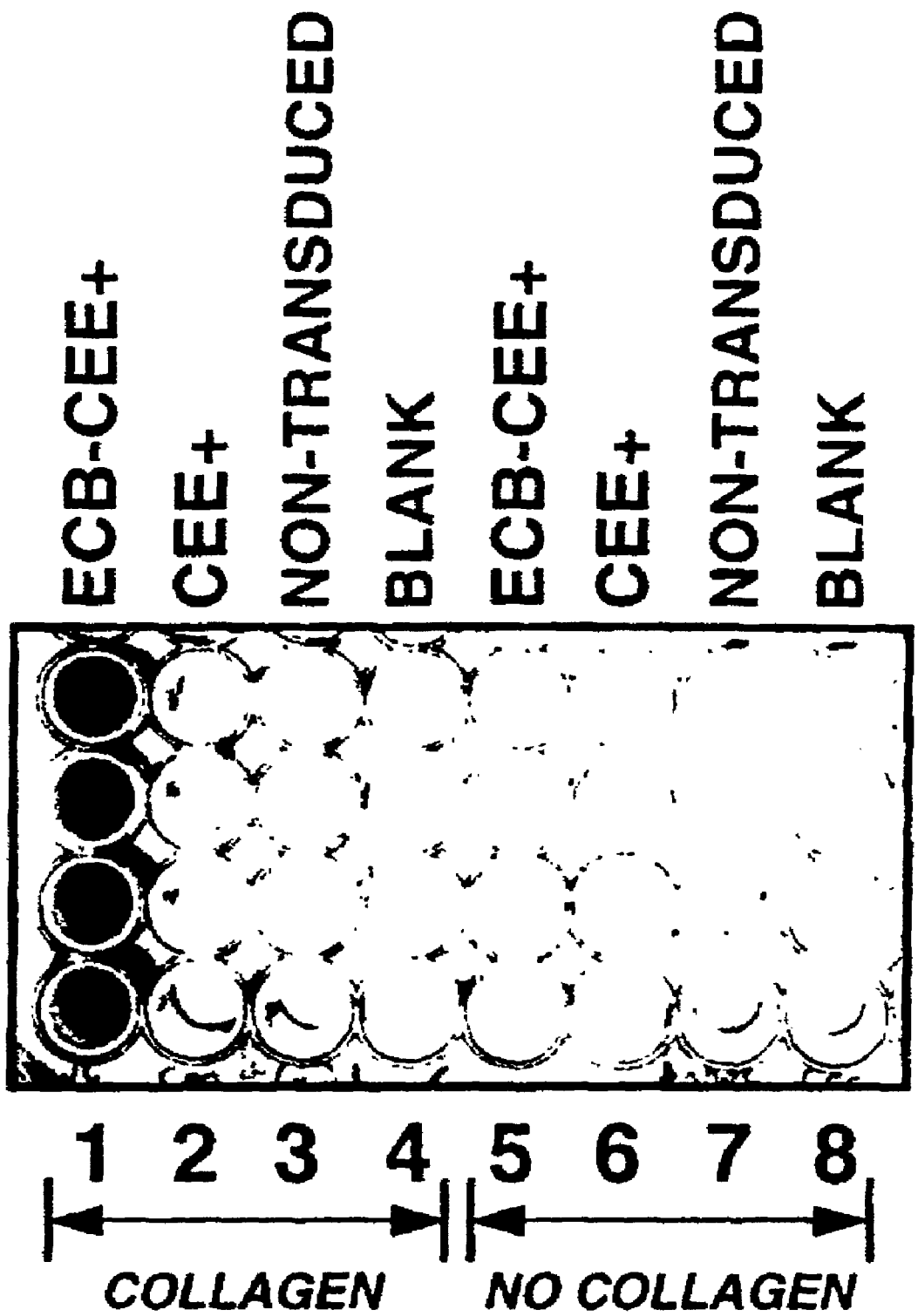

ECB-CB+ was transfected into GPL (Morgan, et al., 1993) and 293T (Pear, et al., Proc. Nat. Acad. Sci., Vol. 90, pgs. 8392-8396 (September. 1993); PCT Application No. WO94/19478, published Sep. 1, 1994), pre-producer cells by calcium phosphate precipitation, and the expression of the recombinant protein was monitored by immmocytochemical detection, using the 83A25 rat monoclonal antibody (Evans, et al., J. Virol, Vol. 64, No. 12, pgs. 6176-6183 (1990)) directed against the Moloney Murine Leukemia Virus env protein. Expression of the chimeric envelope protein bearing the auxiliary collagen-binding domain was confirmed by immunocytochemical staining in both GPL and 293 cells (FIGS. 3A, 3B, and 3C). FIG. 3A shows mock transfected GPL cells-exhibiting no positive staining for gp70 envelope protein. FIG. 3B shows GPL cells transfected with CrR+ (expressing wild type gp70). Brownish staining of the gp70 env protein in shown within the transfected cells. FIG. 3C shows GPL cells transfected with the chimeric ECB-CEE+ env placid DNA. Positive staining for the chimeric gp70 protein is shown within the transfected cells. Thus, the insertion of a collagen-binding sequence into the gp70 sequence did not inhibit expression of the envelope protein in transfected cells. In 293T cells, cell surface expression of the chimeric env protein was detected by immunofluorescence using fluorescence activated cell sorting (FACS) analysis. (Kadan, et al., J. Virol., Vol. 66, pg. 2281 (1992); Morgan, et al., J. Virol., Vol. 67, pg. 4712 (1993); Yu, et al., J. Virol., Vol. 69, pg. 6557 (1996)). The expression of the chimeric gp70 protein also was confirmed by Western analysis (FIG. 3D). The Western Blot shows co-migration of the chimeric ECB-CE+env protein with the wild type CEE+env protein (Mn of approximately 70 kDa bands), as well as co-migration of the gag proteins in the 30 kDa region.

In order to generate retroviral stocks for further study, a transient three plasmid co-transfection system (Soneoka, et al., Nucleic Acids Research, Vol. 23, pgs. 628-633 (1995)) was employed. 10 μg each of (i) pHIT60; (ii) pHIT110 or pHIT112; and (iii) CEE+ or ECB-CEE+ were delivered by transient transfection of 70% confluent 293T cells expressing SV40 T-antigen in 10 cm culture dishes using calcium phosphate for 14-18 hours at 37° C., 5% $CO_2$. Plasmid pHIT60, provided by Dr. Paula Cannon, University of Oxford, Oxford, United Kingdom, includes the SV40 origin of replication and the retroviral gag-pol gene under the control of a cytomegalovirus (CKV) promoter. Plasmid pHIT110, also provided by Dr. Paula Cannon, includes a B-galactosidase (LacZ) gene under the control of a CMV promoter. Plasmid pHIT112, provided by Ling Li, USC Gene Therapy Laboratories, Los Angeles, Calif., also includes a LacZ gene under the control of a CMV promoter. Plasmids pHIT60, pHIT110, and pHIT112 are described further in Soneoka, et al. The cultures then were treated with 6 ml of 10 mM sodium butyrate for 10 to 12 hours to optimize viral production. (Soneoka, et al.) The medium then was replaced with D10 and cultures were maintained at 37° C. for another 12 hours before harvesting the viral supernatants.

Viral titers were determined based on expression of the neomycin resistance and/or the β-galactosidase reporter genes. $2.5 \times 10^4$ NIH 3T3 cells were plated in each of 6-well plates one day prior to transduction. The medium was replaced with 1 ml of serial dilutions of viral supernatant with 8 μg/ml Polybrene for 2 hours, after which 1 ml of fresh D10 was added to the cultures, which then were maintained overnight at 37° C., 5% $CO_2$, after which G418 (800 μg/ml) was added and G418-resistant colonies were counted 10 days later and expressed as G418-resistant colony-forming units (cfu)/ml. For expression of β-galactosidase, the respective cultures were stained with X-gal 48 hours after transduction of NIH 3T3 cells.

Figure 4A:
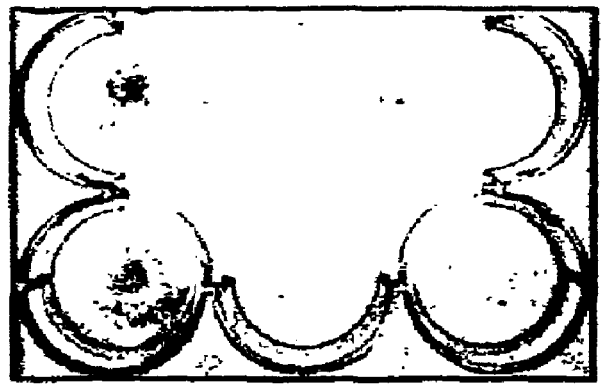
FIG. 4A shows a cell culture plate showing positive staining for β-galactosidase in cultures transduced with viruses bearing the chimeric ECB-CEE+ envelope protein, and negative staining in cultures transduced with wild-type CEE+, and in non-transduced cultures.
Figure 4B:
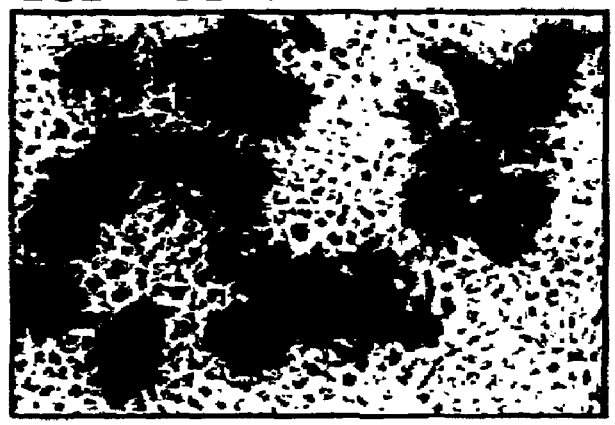
FIG. 4B shows NIH 3T3 cells at high magnification expressing β-galactosidase after transduction by the collagen-bound vector bearing the chimeric ECB-CEE+envelope.

Simultaneous introduction of the above-mentioned plasmids into 293T cells expressing the SV40 T-antigen, followed by sodium butyrate treatment produced retroviral vector titers up to $8 \times 10^6$ cfu/ml, as determined by $neo^r$ and β-galactosidase expression in Nr 3T3 cells. Suspended in cell culture supernatant, the viruses containing the chimeric envelope sequence exhibited titers approaching that of wild-type virus under standardized conditions (relative titers: 0.66±0.42 of wild type, using pHIT110, n=4; 0.53±0.45 using a nuclear-targeted β-galactosidase vector, pcnBg, n=3), indicating that the incorporation of the auxiliary collagen-binding domain did not impair substantially the infectivity of the modified virus. The ECB-CEE+ viruses were collected and the affinity for collagen matrices was evaluated in comparison to wild-type CEE+ viruses, using a modification of standard ELISA techniques. In the ELISA assay, 50 μl of vector supernatant (virus titer of $3.2 \times 10^3$ cfu/ml for ECB-CEE+ and $5.2 \times 10^4$ cfu/ml for CEE+) was applied to each collagen-coated microtiter well and allowed to bind for 20 minutes, followed by washing with 1×PBS, followed by incubation for 4 ho at room temperature at a primary antibody dilution of 1:1,000. A biotinylated goat antibody to rat IgG then was applied followed by a streptavidin-horseradish peroxide conjugate. Diaminobenzidine (DAB) was used as a chromogen followed by nickel chloride enhancement for microtiter plates. After simple washing with physiological saline, only the viruses bearing the chimeric env protein remained bound to collagen (Lane 1, dark staining wells) upon washing with PBS, while the wild type CEE+ virions were removed. (FIG. 3B.) The capability of collagen matrices to concentrate the ECB-CEE+ retroviral vectors from dilute solutions was examined first by applying retroviral supernatant to collagen coated 6-well culture plates, washing the culture plates with physiological saline, and then seeding a monolayer of cells onto the washed plates. Specifically, 1.5 ml of vector supernatant bearing ECB-CEE+, wild-type CEE+, or buffer (viral titer:$4.4 \times 10^3$ cfu/ml for ECB-CEE+ and $9.1 \times 1^4$ for CEE+) were incubated at 37° C. in 6-well plates in which an island of collagen was applied (within a cloning ring), and washed twice with 1×PBS. $1 \times 10^6$ NIH 3T3 cells, suspended in DMEM-10% FBS medium containing 8 Ag/ml Polybrene then were plated into each well. The cultures were incubated at 37° C. overnight, replaced with D10 medium not containing Polybrene, and stained with X-Gal after an additional 24 hours of incubation at 37° C. As shown in FIG. 4A, the collagen-targeted retroviral vector remained bound to the collagen matrix under conditions in which the wild-type CEE+ was washed away. From the transduction efficiencies (20-40%) observed in the NIH 3T3 cells overlaid upon the virus-bound collagen (FIG. 4B), the concentration effect observed under these conditions was at least two orders of magnitude greater than the assayed titer of the original supernatants.

Based on previous observations that the biological half-life of collagen-targeted TGF-β fusion protein (Tuan, et al., *Conn. Tiss. Res.*, Vol. 34, pgs. 1-9 (1996)) may be extended by the physical association with collagen, it was anticipated that the collagen-targeted retroviral vectors also may gain resistance to inactivation by serum components. The comparative infectivity of ECB-CEE+ virions in the presence of normal human serum under standardized conditions was examined. NIH 3T3 cells were assayed for β-galactosidase expression 48 hours following transduction with the ECB-CEE+ vector or ECB-CEE+ in suspension. Prior to the transduction of NIH 3T3 cells, collagen-bound ECB-CEE+ virions and ECB-CEE+ virions in suspension were exposed to 10% normal human serum for various time periods, followed by complement inactivation at 50° C. for 30 minutes.

More particularly, 50 μl of ECB-CEE+ supernatant were applied three times to each collagen-coated well and the viruses were incubated at 37° C. for 30 minutes. Then, the collagen-bound vector was exposed to 10% normal human serum for various time periods, after which $1 \times 10^3$ cells in D10, containing 8 μg/ml Polybrene, were plated for 2 hours. After replacement with fresh D10 medium, the cultures were incubated at 37° C. in 5% for 48 hours after which the cultures were stained with X-gal stain. For comparison, 50 μl of ECB-CEE+ supernatant (ECB-CEE+ in suspension) initially were exposed to 10% normal human serum for various time periods after which the samples were heated to 50° C. to inactivate complement, and then applied to $1 \times 10^3$ cells in non-coated wells, in the presence of 8 μg/ml Polybrene overnight. Medium then was replaced with fresh D10 medium, and cultures were maintained for 48 hours prior to X-gal staining. Transduction efficiency was determined by counting the number of cells with blue-staining nuclei in a total of 300 cells. Results are expressed as percent of transduction efficiency prior to incubation with normal human serum which parallels that with heat-inactivated serum (n=3 for each group). The significance of difference between the two groups was tested by the Student's t-test. Transduction efficiency of ECB-CEE+ virions on collagen was greater than ECB-CEE+ virions in suspension at 1 or 2 minutes of incubation with serum.

Figure 4C:
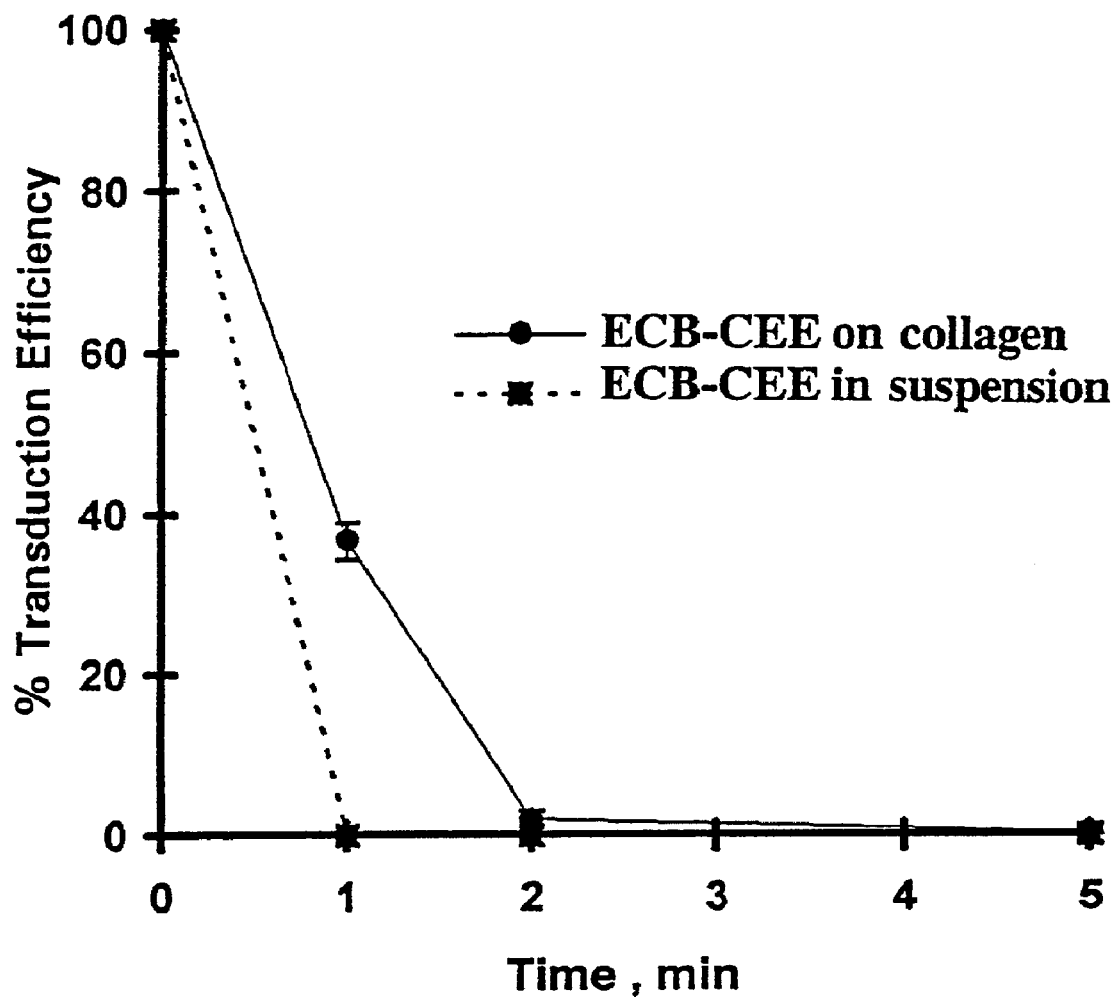
FIG. 4C is a graph of the transduction efficiency of viruses bearing the chimeric ECB-CEE+ protein in the presence of normal human serum.
Figure 5:
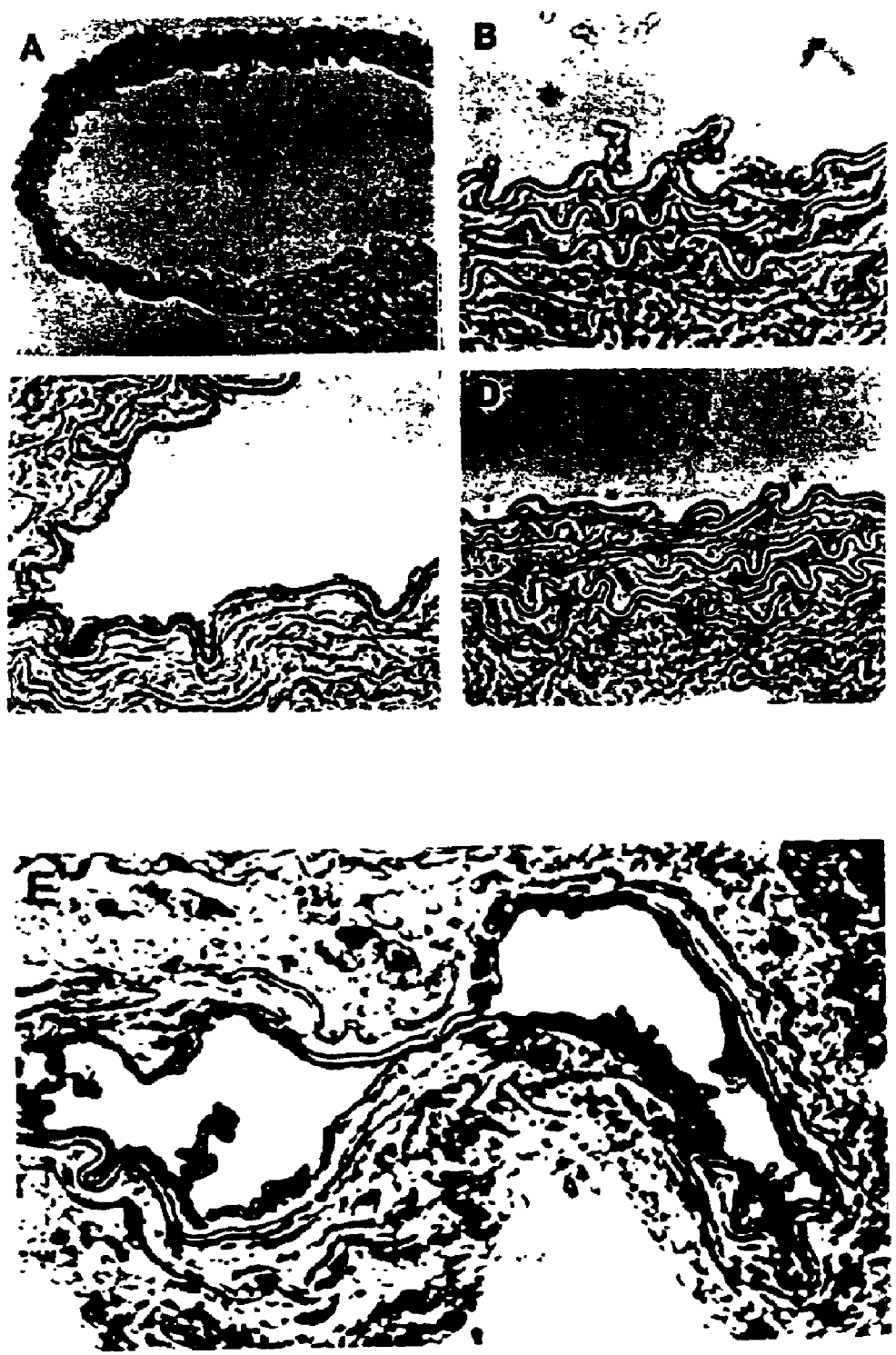
FIG. 5A shows an untreated catheter-injured segment of mouse aorta.
FIG. 5B shows a higher magnification of a portion of the catheter-injured segment shown in FIG. 5A.
FIG. 5C depicts binding of the ECB-CEE+ chimeric envelope protein to an injured segment of mouse aorta.
FIG. 5D shows the absence of binding of the ECB-CEE+ chimeric envelope protein to a non-injured segment of mouse aorta.
FIG. 5E shows binding of the ECB-CEE+ chimeric envelope protein to an injured inferior vena cava segment.
FIG. 5F shows in vivo transduction of chondrocytes by an ECB-CEE+ virus as demonstrated by expression of nuclear targeted β-galactosidase after injection of vector supernatant into the tail of a newborn mouse.

In contrast to the wild-type virus which is inactivated rapidly by serum components (Bartholomew, et al., *J. Exp. Med.*, Vol. 147, pgs. 844-853 (1978); Rother, et al., *J. Exp. Med.*, Vol. 182, pgs. 1345-1355 (1995); Pensiero, et al., *Human Gene Therapy*, Vol. 7, pgs. 1095-1101 (1996)), the ECB-CEE+ virions were more resistant, exhibiting appreciable transduction efficiencies in the presence of normal human serum. (FIG. 4C) Whereas the wild-type virus and ECB-CEE+ virions in suspension were inactivated within one minute of exposure to 10% normal human serum, the infectivity of the collagen-bound virions was diminished but not abolished. The resistance of the ECB-CEE+ virions to serum inactivation was found to be dependent upon their binding to collagen, rather than the modification of the envelope protein itself, was responsible for this selective protection.

Example 2

A major advantage of gene therapy over conventional pharmacological therapy for cardiovascular disease is the potential that transduction of vascular cells at specific sites will result in localized cellular effects and/or sustained levels of protein production in target vascular cells. (Feldman, et al., *Cardiovascular Res*., Vol. 32, pgs. 194-207 (1996); Gibbons, et al., *N. Engl. J. Med*., Vol. 330, pgs. 1431-1438 (1994).) Restenosis following vascular injury represents a leading target for cardiovascular gene therapy on the basis of its high incidence (Glagov, *Circulation*, Vol. 89, pgs. 2888-2891 (1994); Schwartz, et al., *Am. Coll. Cardiol*., Vol. 17, pg. 1284 (1992); Myers, *Wound Healing Responses in Cardiovascular Disease*, Weber, ed., Futura Publishing Co., Mt. Kisco, N.Y., pgs. 137-150 (1995)) and refractoriness to conventional approaches (Hermans, et al., *Am. Heart J*., Vol. 122, pgs. 171-187 (1991); Popma, et al., *Circulation*, Vol. 84, pgs. 1426-1436 (1991); Feldman, et al., *Fundam. Clin. Pharmacol*., Vol. 9, pgs. 8-16 (1995)). In order to investigate the binding properties of the chimeric envelope protein to injured vis-a-vis non-injured vasculature, the purified, renatured SU-ECB-CEE+ chimeric envelope protein was applied to a segment of normal mouse aorta or inferior vena cava (IVC) and to aortic or venous segments therein the endothelial layer had been denuded by the passage of a catheter. More specifically, segments of aorta and inferior vena cava were isolated, and the lumens were washed with physiologic saline to remove blood elements. The endothelium was denuded by several passages with a 2F Intimax embolectomy catheter, inflated to a volume of 10 μl, through the lumen of the vessel segments. 50 μl of the purified chimeric envelope protein or buffer (control) then was instilled into the lumen for 30 minutes at room temperature. The lumens of the vessel segments then were washed twice with physiological saline, and the isolated segments then were placed in microfuge tubes containing 200 μl of chimeric envelope protein or buffer for another 30 minutes at room temperature. SU-ECB-CEE+ treated and untreated segments were frozen quickly in liquid nitrogen, and cryostat sections were fixed in acetone for immunohistochemical staining to detect the collagen-bound chimeric envelope protein. FIG. 5A shows a catheter-injured aortic segment that was not treated. FIG. 5B shows a higher magnification of the segment shown in FIG. 5A. FIG. 5C shows binding of the chimeric SU-ECB-CEE+ envelope protein (red-staining material) to an injured aortic segment. FIG. 5D shows the absence of chimeric envelope protein binding in a non-injured treated aortic segment. FIG. 5E shows binding of the chimeric envelope protein (red-staining material) to an injured inferior vena cave segment. In these experiments, about 1 μg of renatured SU-ECB-CEE+ protein was instilled into the injured and non-injured aortic segments followed by flushing with physiological saline. The injured and non-injured segments then were frozen in liquid nitrogen, and acetone-fixed cryostat sections then were subjected to immunocytochemical analysis, using the 82A25 monoclonal antibody to gp70 and an immunoperoxidase detection system.

Collagen-coated microtiter plates and cryostat sections of treated or untreated, injured or non-injured aortic or inferior vena cava segments were incubated for 4 hours at room temperature at a primary antibody dilution of 1:1,000. A biotinylated goat antibody to rat IgG then was applied, followed by a strepavidin-horseradish peroxidase conjugate. Diaminobenzidine (DAB) was used as a chromogen, followed by nickel chloride enhancement for microtiter plates. Histological slides were counterstained with hematoxylin.

As shown in FIGS. 5A through 5D, the collagen-targeted SU-ECB-CEE+ envelope protein bound selectively to the subendothelial layer exposed by catheter injury and did not bind to the non-injured aortic segment. Likewise, the chimeric envelope protein bound selectively to the subendothelium of the injured vena cava (FIG. 5S).

Figure 5F:
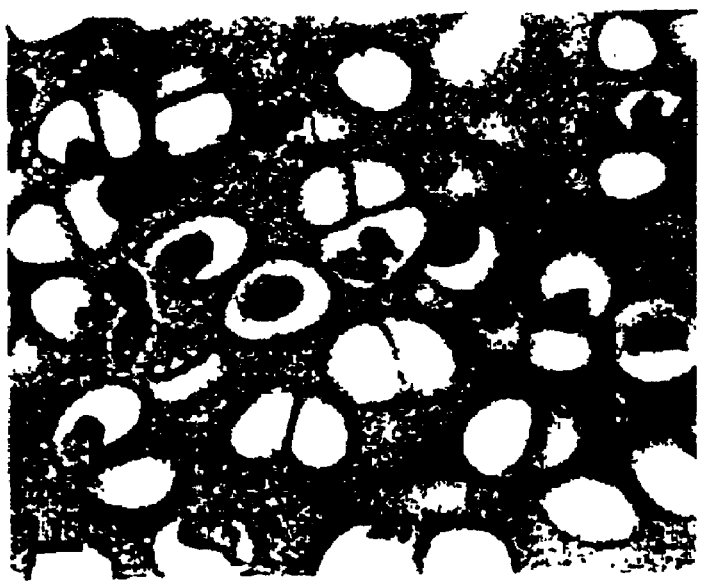

The infectivity of ECB-CEE+virions was demonstrated for the first time In vivo in the proliferative tissues of a newborn mouse. FIG. 5F shows the in vivo transduction by ECB-CEE+ virions by the expression of the nuclear-targeted B-galactosidase transgene in chondrocytea (blue staining nuclei) after injection of vector supernatant (titer=$1\times10^3$) into the tail of a newborn mouse.

Figure 6:
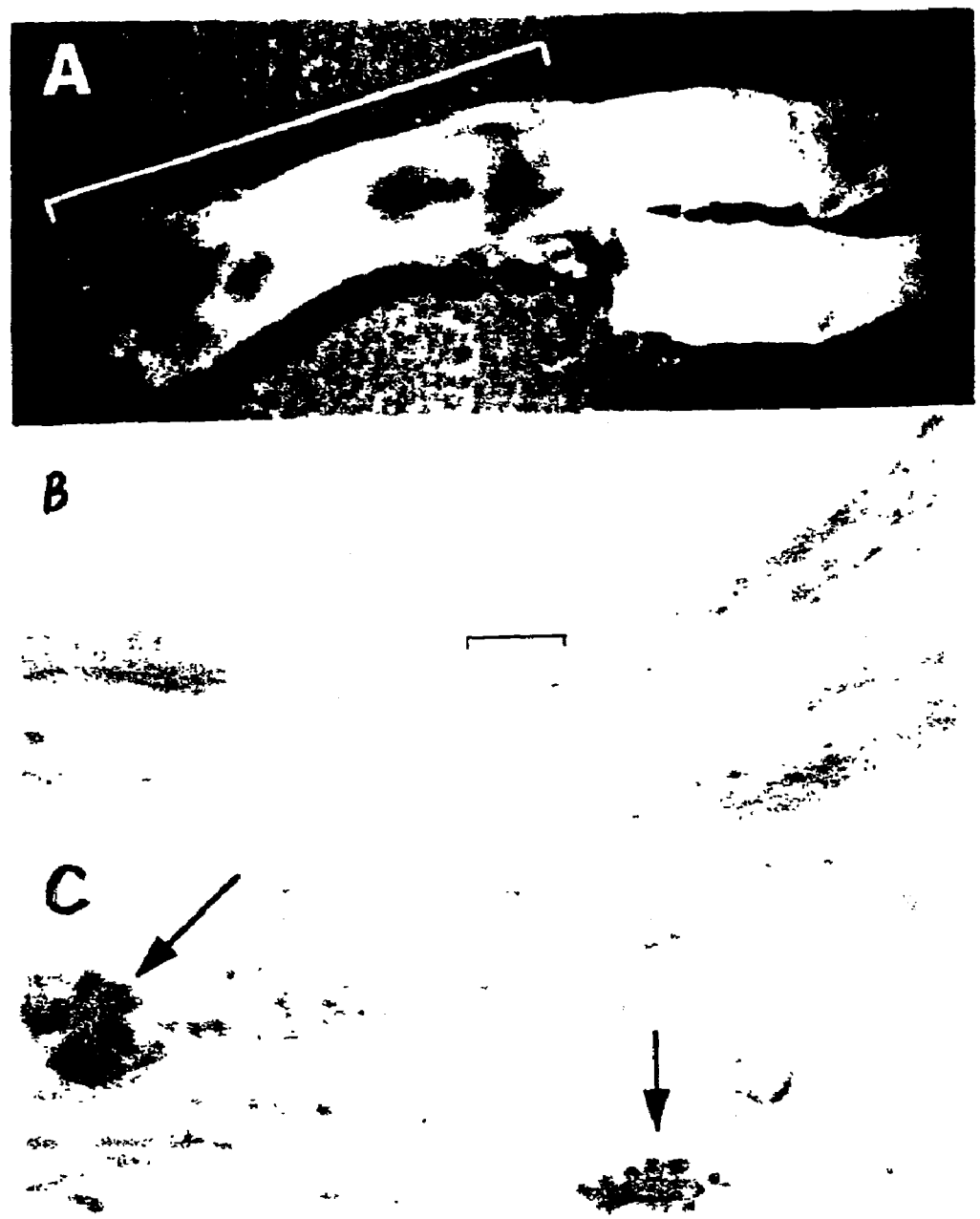
FIG. 6A shows the gross appearance of a segment of the left common carotid artery (dissected longitudinally) of a rat at 9 days after balloon catheter injury and 2 days after instillation of ECB-CEE+ vector supernatant (titer: $8 \times 10^5$ cfu/ml). The bracketed area shows the actual site of vascular injury and in vivo transduction. The arterial segment to the right of the bracketed area was not injured but was exposed to the same vector. A short segment of the right carotid artery is shown (lower right) as a non-injured, untreated control.
FIG. 6B shows low power (10×) magnification of a formalin-fixed longitudinal section of an injured rat common carotid artery, following x-gal staining. Numerous cells (arrows) with blue-staining nuclei are noted along the length of the tunica media.
FIG. 6C shows high power magnification of a segment of arterial wall (bracketed area in FIG. 6B showing smooth muscle cells expressing the nuclear-targeted β-galactosidase transgene (arrows point to cells with prominent blue nuclei).

In order to investigate further the performance of the collage-targeted retroviral vector in vivo, the transduction of vascular cells following balloon catheter injury in a rat model of vascular restenosis was examined. Under general anesthesia (ketamine, 10 mg/kg; rompun, 5 mg/kg) in accordance with a protocol approved by the USC Institution Animal Care and Use Caomittee, a 2F Intimax arterial embolectomy catheter (Applied Medical Resources Corp., Laguna Hills, Calif.) was used to denude the carotid artery endothelium of Wistar rats (each weighing 400 to 500 grams). The catheter was inserted into an external carotid artery which was ligated distally, and passed into the common carotid artery. The balloon was inflated to a volume of 10 µl and passed three times along the length of the common carotid artery. After the balloon injury, the embolectomy catheter was removed and the internal carotid artery was ligated transiently just distal to the bifurcation. The distal half of the injured segment likewise was ligated transiently. Bach rat received an infusion of ECB-CEE+vector supernatant (titers: $2\times10^4$ to $8\times10^x$ cfu/ml) at 4 to 7 days after balloon injury after which the rats were allowed to recover, and fed a regular mouse/rat diet and water ad libitum. The rats were sacrificed at the specified time by an overdose of sodium pentobarbital (120 mg/kg intramuscularly), and frozen sections of injured carotid artery were stained with X-gal and Siris red stain. Histological sections were examined by light microscopy, for expression of nuclear-targeted β-galactosidase. As shown in FIG. 6A, transduction of the arterial wall was limited to the site of vascular injury (bracketed area). Histochemical analysis of formalin-fixed arterial segments (FIG. 6B) revealed extensive penetration of the vector into the tunica media of the injured artery, evidenced by the transduction of numerous smooth muscle cells. (FIGS. 6B and 6C.) These observations, in principle, demonstrate the utility of genetically engineered retroviral envelope proteins to localize viral delivery to a specific locus of vascular injury.

Discussion

Previous studies demonstrated the feasibility of utilizing retroviral vectors for direct gene transfer into arterial wall (Nabel, et al., *Science*, Vol. 249, pgs. 1285-1288 (1990); Flugelman, et al., *Circulation*, Vol. 85, pgs. 1110-1117 (1992); Wilson et al., *Science*, Vol. 244, pgs. 1344-1346 (1989); Dichek, et al. *Blood*, Vol. 77, pgs. 533-541 (1991)). The transduction efficiency, however, was found to be low (<0.1%), due partly to the low rate of cell proliferation (required for retroviral integration) found in the normal intact arterial wall and to the inability to obtain adequate amounts of high titer (>$1\times10^6$ particles/ml) retroviral stocks required for efficient gene transfer (Nabel, *Circulation*, Vol. 91, pgs. 541-549 (1995)). The above examples describe the construction and performance of a collagen-targeted retroviral vector that remains stable and infectious upon collagen binding. The physical association of the chimeric virion envelope protein with collagen has ramifications in vitro and in vivo: In vitro, in terms of affinity purification and concentration of virus stocks from dilute solutions, and in vivo, in terms of boosting the concentration-dependent delivery of therapeutic genes. The data support the concept that the components of the extracellular matrix itself may be advantageous target components in future gene delivery strategies. Nonspecific binding of retroviral particles to fibronectin fragments has been shown to increase the transduction efficiency of mammalian cells (Henenberg, et al. *Nature Medicine*, Vol. 2 pgs. 876-882 (1996)). High affinity targeting of growth factors (Tuan et al. *Conn. Tiss. Res*., Vol. 34, pgs. 1-9 (1996)) and retroviral vectors to fibronectin may be used to facilitate gene delivery in the clinical management of wound healing. The above examples also show that the close association with collagen rendered the virion less sensitive to inactivation by human serum, which occurs presumably via complement-mediated mechanisms (Bartholomew et al., *J. Exp. Med*. Vol. 147, pgs. 844-853 (1978); Rother et al., *J. Exp. Med*; Vol. 182 pgs. 1345-1355 (1995); Pensiero, et al., *Human Gene Therapy*, Vol. 7, pgs. 1095-1101 (1995)). This property of complement resistance may be a considerable utility in the design of future injectable vectors.

Initially identified as a hemostatic factor in studies of inherited hemophilias (Wagner, *Ann. Rev. Cell Biol*. Vol. 6, pg. 217 (1990); Montgomery and Scott, *Hematology of Infancy and Childhood*; Nathan, et al. eds., Philadelphia, W. B Saunders, Vol. 2, Ed. 4, pgs. 1605-1650 (1993)), von Willebrand factor performs a vital surveillance function by targeting platelet aggregates to vascular lesions (Ginsburg and Bowie, *Blood*, Vol. 70, pgs. 2507-2519 (1992)). The transposition of a collagen binding domain in derived from von Willebrand factor to alter the distribution, concentration, and stability of retroviral gene delivery vectors was demonstrated in the above examples. These collagen-targeted vectors may be used to increase the efficiency of localized gene transfer, delivering therapeutic genes to restore endothelial cell function and to combat thrombosis, in addition to limiting the proliferative and fibrotic responses associated with neointima formation. The above mentioned targeted vectors could also have important implications in the design and efficacy of systemic gene therapy strategies. The application of high efficiency targeting vectors that, like von Willebrand factor itself, perform a surveillance function within the vasculature may represent a major advancement in the potential to treat coronary artery disease and stroke. In that collagen is exposed by traumatic, inflammatory, ulcerative, and metastatic lesions, as well as sites of surgical intervention, these targeted retroviral vectors provide new approaches to advance gene therapy in other areas of surgical intervention.

The disclosures of all patents, publications (including published patent applications), database accession numbers, and depository accession numbers referenced in this specification are specifically incorporated herein by reference in their entirety to the same extent as if each such individual patent, publication, database accession number, and depository accession number were specifically and individually indicated to be incorporated by reference.

It is to be understood, however, that the scope of the present invention is not to be limited to the specific embodiments described above. The invention may be practiced other than as particularly described and still be within the scope of the accompanying claims.

SEQUENCE LISTING (1) GENERAL INFORMATION:
(i) APPLICANT: Hall, Frederick L.
Gordon, Erlinda M.
Anderson, W. French
Starnes, Vaughn A.
(ii) TITLE OF INVENTION: Modified Retroviral Envelope Polypeptides for Binding to Extracellular Matrix Components
(iii) NUMBER OF SEQUENCES: 3
(iv) CORRESPONDENCE ADDRESS:
(A) ADDRESSEE: Carella, Byrne, Bain, Gilfillan, Cecchi, Stewart & Olstein
(B) STREET: 6 Becker Farm Road
(C) CITY: Roseland
(D) STATE: New Jersey
(E) COUNTRY: USA
(F) ZIP: 07068
(v) COMPUTER READABLE FORM:
(A) MEDIUM TYPE: 3.5 inch diskette
(B) COMPUTER: IBM PS/2
(C) OPERATING SYSTEM: MS-DOS
(D) SOFTWARE: Word Perfect 5.1
(vi) CURRENT APPLICATION DATA:
(A) APPLICATION NUMBER:
(B) FIXING DATE:
(C) CLASSIFICATION:
(vii) PRIOR APPLICATION DATA:
(A) APPLICATION NUMBER:
(B) FILING DATE:
(viii) ATTORNEY/AGENT INFORMATION:
(A) NAME: Olstein, Elliot M.
(B) REGISTRATION NUMBER: 24,025
(C) REFERENCE/DOCKET NUMBER: 271010-364
(ix) TELECOMMUNCIATION INFORMATION:
(A) TELEPHONE: 201-994-1700
(B) TELEFAX: 201-994-1744
(2) INFORMATION FOR SEQ ID NO: 1:
(i) SEQUENCE CHARACTERISTICS:
(A) LENGTH: 229 amino acids
(B) TYPE: amino acids
(C) STRANDEDNESS:
(D) TOPOLOGY: linear
(ii) MOLECULE TYPE: polypeptide
(ix) FEATURE:
(A) NAME/KEY: Receptor binding region of ecotropic gp70 protein
(xi) SEQUENCE DESCRIPTION: SEQ ID NO:1:

| | | | | | | | | | |
|---|---|---|---|---|---|---|---|---|---|
| Ala | Ser | Pro | Gly | Ser | Ser | Pro | | | |
| | | | | 5 | | | | | |
| His | Gln | Val | Tyr | Asn | Ile | Thr | Trp | Glu | Val |
| | | 10 | | | | | 15 | | |
| Thr | Asn | Gly | Asp | Arg | Glu | Thr | Val | Trp | Ala |
| | | 20 | | | | | 25 | | |
| Thr | Ser | Gly | Asn | His | Pro | Leu | Trp | Thr | Trp |
| | | 30 | | | | | 35 | | |
| Trp | Pro | Asp | Leu | Thr | Pro | Asp | Leu | Cys | Met |
| | | 40 | | | | | 45 | | |
| Leu | Ala | His | His | Gly | Pro | Ser | Tyr | Trp | Gly |
| | | 50 | | | | | 55 | | |
| Leu | Gly | Tyr | Gln | Ser | Pro | Phe | Ser | Ser | Pro |
| | | 60 | | | | | 65 | | |
| Pro | Gly | Pro | Pro | Cys | Cys | Ser | Gly | Gly | Ser |
| | | 70 | | | | | 75 | | |
| Ser | Pro | Gly | Cys | Ser | Arg | Asp | Cys | Glu | Glu |
| | | 80 | | | | | 85 | | |
| Pro | Leu | Thr | Ser | Leu | Thr | Pro | Arg | Cys | Asn |
| | | 90 | | | | | 95 | | |
| Thr | Ala | Trp | Asn | Arg | Leu | Lys | Leu | Asp | Gln |
| | | 100 | | | | | 105 | | |
| Thr | Thr | His | Lys | Ser | Asn | Glu | Gly | Phe | Tyr |
| | | 110 | | | | | 115 | | |
| Val | Cys | Pro | Gly | Pro | His | Arg | Pro | Arg | Glu |
| | | 120 | | | | | 125 | | |
| Ser | Lys | Ser | Cys | Gly | Gly | Pro | Asp | Ser | Phe |
| | | 130 | | | | | 135 | | |

| | | | | | | | | | |
|---|---|---|---|---|---|---|---|---|---|
| Tyr | Cys | Ala<br>140 | Tyr | Trp | Gly | Cys | Glu<br>145 | Thr | Thr |
| Gly | Arg | Ala<br>150 | Tyr | Trp | Lys | Pro | Ser<br>155 | Ser | Ser |
| Trp | Asp | Phe<br>160 | Ile | Thr | Val | Asn | Asn<br>165 | Asn | Leu |
| Thr | Ser | Asp<br>170 | Gln | Ala | Val | Gln | Val<br>175 | Cys | Lys |
| Asp | Asn | Lys<br>180 | Trp | Cys | Asn | Pro | Leu<br>185 | Val | Ile |
| Arg | Phe | Thr<br>190 | Asp | Ala | Gly | Arg | Arg<br>195 | Val | Thr |
| Ser | Trp | Thr<br>200 | Thr | Gly | His | Tyr | Trp<br>205 | Gly | Leu |
| Arg | Leu | Tyr<br>210 | Val | Ser | Gly | Gln | Asp<br>215 | Pro | Gly |
| Leu | Thr | Phe<br>220 | Gly | Ile | Arg | Leu | Arg<br>225 | Tyr | Gln |
| Asn | Leu | | | | | | | | |

(2) INFORMATION FOR SEQ ID NO: 2:
    (i) SEQUENCE CHARACTERISTICS:
        (A) LENGTH: 687 bases
        (B) TYPE: nucleic acid
        (C) STRANDEDNESS: single
        (D) TOPOLOGY: linear
    (ii) MOLECULE TYPE: polynucleotide
    (ix) FEATURE:
        (A) NAME/KEY: polynucleotide encoding receptor
            binding region of ecotropic gp70
            protein
    (xi) SEQUENCE DESCRIPTION: SEQ ID NO: 2:

```
GCTTCGCCCG GCTCCAGTCC TCATCAAGTC TATAATATCA CCTGGGAGGT AACCAATGGA    60
GATCGGGAGA CGGTATGGGC AACTTCTGGC AACCACCCTC TGTGGACCTG GTGGCCTGAC   120
CTTACCCCAG ATTTATGTAT GTTAGCCCAC CATGGACCAT CTTATTGGGG GCTAGAATAT   180
CAATCCCCTT TTTCTTCTCC CCCGGGGCCC CCTTGTTGCT CAGGGGGCAG CAGCCCAGGC   240
TGTTCCAGAG ACTGCGAAGA ACCTTTAACC TCCCTCACCC CTCGGTGCAA CACTGCCTGG   300
AACAGACTCA AGCTAGACCA GACAACTCAT AAATCAAATG AGGGATTTTA TGTTTGCCCC   360
GGGCCCCACC GCCCCCGAGA ATCCAAGTCA TGTGGGGGTC CAGACTCCTT CTACTGTGCC   420
TATTGGGGCT GTGAGACAAC CGGTAGAGCT TACTGGAAGC CCTCCTCATC ATGGGATTTC   480
ATCACAGTAA ACAACAATCT CACCTCTGAC CAGGCTGTCC AGGTATGCAA AGATAATAAG   540
TGGTGCAACC CCTTAGTTAT TCGGTTTACA GACGCCGGGA GACGGGTTAC TTCCTGGACC   600
ACAGGACATT ACTGGGGCTT ACGTTTGTAT GTCTCCGGAC AAGATCCAGG CTTACATTT    660
GGGATCCGAC TCAGATACCA AAATCTA                                      687
```

(2) INFORMATION FOR SEQ ID NO: 3:
    (i) SEQUENCE CHARACTERISTICS:
        (A) LENGTH: 10 amino acids
        (B) TYPE: amino acid
        (C) STRANDEDNESS:
        (D) TOPOLOGY: linear
    (ii) MOLECULE TYPE: polypeptide
    (ix) FEATURE:
        (A) NAME/KEY: collagen-binding domain of
            von Willebrand Factor
    (xi) SEQUENCE DESCRIPTION: SEQ ID NO: 3:

| | | | | | | | | | |
|---|---|---|---|---|---|---|---|---|---|
| Trp | Arg | Glu | Pro | Ser<br>5 | Phe | Met | Ala | Leu | Ser<br>10 |

---

SEQUENCE LISTING

<160> NUMBER OF SEQ ID NOS: 15

<210> SEQ ID NO 1
<211> LENGTH: 229
<212> TYPE: PRT
<213> ORGANISM: Moloney murine leukemia virus

<400> SEQUENCE: 1

Ala Ser Pro Gly Ser Ser Pro His Gln Val Tyr Asn Ile Thr Trp Glu
1               5                   10                  15

```
Val Thr Asn Gly Asp Arg Glu Thr Val Trp Ala Thr Ser Gly Asn His
        20                  25                  30

Pro Leu Trp Thr Trp Trp Pro Asp Leu Thr Pro Asp Leu Cys Met Leu
            35                  40                  45

Ala His His Gly Pro Ser Tyr Trp Gly Leu Glu Tyr Gln Ser Pro Phe
    50                  55                  60

Ser Ser Pro Pro Gly Pro Pro Cys Cys Ser Gly Ser Ser Pro Gly
65                  70                  75                  80

Cys Ser Arg Asp Cys Glu Glu Pro Leu Thr Ser Leu Thr Pro Arg Cys
                85                  90                  95

Asn Thr Ala Trp Asn Arg Leu Lys Leu Asp Gln Thr Thr His Lys Ser
            100                 105                 110

Asn Glu Gly Phe Tyr Val Cys Pro Gly Pro His Arg Pro Arg Glu Ser
        115                 120                 125

Lys Ser Cys Gly Gly Pro Asp Ser Phe Tyr Cys Ala Tyr Trp Gly Cys
    130                 135                 140

Glu Thr Thr Gly Arg Ala Tyr Trp Lys Pro Ser Ser Ser Trp Asp Phe
145                 150                 155                 160

Ile Thr Val Asn Asn Asn Leu Thr Ser Asp Gln Ala Val Gln Val Cys
                165                 170                 175

Lys Asp Asn Lys Trp Cys Asn Pro Leu Val Ile Arg Phe Thr Asp Ala
            180                 185                 190

Gly Arg Arg Val Thr Ser Trp Thr Thr Gly His Tyr Trp Gly Leu Arg
        195                 200                 205

Leu Tyr Val Ser Gly Gln Asp Pro Gly Leu Thr Phe Gly Ile Arg Leu
    210                 215                 220

Arg Tyr Gln Asn Leu
225

<210> SEQ ID NO 2
<211> LENGTH: 687
<212> TYPE: DNA
<213> ORGANISM: Moloney murine leukemia virus

<400> SEQUENCE: 2
gcttcgcccg ctccagtcc tcatcaagtc tataatatca cctgggaggt aaccaatgga      60
gatcgggaga cggtatgggc aacttctggc aaccaccctc tgtggacctg gtggcctgac     120
cttaccccag atttatgtat gttagcccac catggaccat cttattgggg ctagaatat     180 caatccccct tttcttctcc cccggggccc ccttgttgct caggggcag cagcccaggc     240 tgttccagag actgcgaaga acctttaacc tccctcaccc ctcggtgcaa cactgcctgg     300
aacagactca agctagacca gacaactcat aaatcaaatg agggattta tgtttgcccc     360 gggcccacc gccccgaga atccaagtca tgtggggtc cagactcctt ctactgtgcc       420
tattggggct gtgagacaac cggtagagct tactggaagc cctcctcatc atgggatttc     480
atcacagtaa caacaatct cacctctgac caggctgtcc aggtatgcaa agataataag       540
tggtgcaacc cctagttat tcggtttaca gacgccggga gacgggtac ttcctggac       600 acaggacatt actggggctt acgtttgtat gtctccggac aagatccagg gcttacattt     660
gggatccgac tcagatacca aaatcta                                          687

<210> SEQ ID NO 3
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Trp Arg Glu Pro Ser Phe Met Ala Leu Ser
1               5                  10

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Trp Ser His Trp
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Val Pro Arg Gly Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Arg Glu Pro Ser Phe Met Ala Leu Ser
1               5                  10

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tggcgcgaac cgagcttcat ggctctgagc                                     30

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atcacctggg aggtaaccgg ccatatgtgg cgc                                 33

<210> SEQ ID NO 9
```

<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgatctccat tggttaccaa gctagcaccg ct                                    32

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgatctccat tggttaccaa gctgccgcgc ggcaccagac cgctcagagc                 50

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
1               5

<210> SEQ ID NO 12
<211> LENGTH: 6
<212> TYPE: PRT
<213> ORGANISM: Moloney murine leukemia virus

<400> SEQUENCE: 12

Ile Thr Trp Glu Val Thr
1               5

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly His Met Trp Arg Glu Pro Ser Phe Met Ala Leu Ser Gly Ala Ser
1               5                   10                  15

Leu Val Thr

<210> SEQ ID NO 14
<211> LENGTH: 6
<212> TYPE: PRT
<213> ORGANISM: Moloney murine leukemia virus

<400> SEQUENCE: 14

Asn Gly Asp Arg Glu Thr
1               5

<210> SEQ ID NO 15
<211> LENGTH: 29

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggtgctagct tggtaaccaa tggagatcg                                   29
```

What is claimed is:

1. A retroviral particle, comprising:

i) a modified retroviral envelope protein wherein the retroviral envelope protein includes a receptor binding region, wherein the receptor binding region is modified to include a collagen binding domain, and ii) at least one desired transgene operably linked to a promoter, wherein the retroviral particle, when delivered to a mammal having a site of tissue injury, binds to collagen exposed at the site of tissue injury, and expresses the desired transgene at the site of tissue injury and wherein the titer of the retroviral particle is at least $1\times10^4$ cfu/ml.

2. A retroviral particle, comprising:

i) a modified retroviral envelope protein wherein the retroviral envelope protein includes a receptor binding region, wherein the receptor binding region is modified to include a collagen binding domain, and ii) at least one desired transgene operably linked to a promoter, wherein the retroviral particle, when delivered to a mammal having a site of tissue injury, binds to collagen exposed at the site of tissue injury, and expresses the desired transgene at the site of tissue injury and wherein the transgene expresses a therapeutic agent.

3. The retroviral particle according to claim 2, wherein the therapeutic agent is selected from the group consisting of cell cycle control agents, growth factors, cytokines, anticoagulants, anti-platelet agents, anti-inflammatory agents, tumor suppressor proteins, clotting factors, cystic fibrosis transmembrane conductance regulator (CFTR), and negative selective markers.

* * * * *